(12) United States Patent
Demmer et al.

(10) Patent No.: US 11,484,719 B2
(45) Date of Patent: Nov. 1, 2022

(54) ELECTRICAL STIMULATION RATE MODULATION FOR COMMUNICATION OF DATA VALUES IN A MEDICAL DEVICE SYSTEM

(71) Applicant: Medtronic, Inc., Minneapolis, MN (US)

(72) Inventors: Wade M. Demmer, Coon Rapids, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 77 days.

(21) Appl. No.: 16/786,493

(22) Filed: Feb. 10, 2020

(65) Prior Publication Data
US 2020/0254262 A1  Aug. 13, 2020

Related U.S. Application Data

(60) Provisional application No. 62/805,101, filed on Feb. 13, 2019.

(51) Int. Cl.
*A61N 1/37* (2006.01)
*A61N 1/36* (2006.01)
*A61N 1/365* (2006.01)

(52) U.S. Cl.
CPC ....... *A61N 1/3706* (2013.01); *A61N 1/36189* (2013.01); *A61N 1/36592* (2013.01)

(58) Field of Classification Search
None
See application file for complete search history.

(56) References Cited

U.S. PATENT DOCUMENTS

| | | | |
|---|---|---|---|
| 5,507,782 A | 4/1996 | Kieval et al. |
| 5,899,928 A | 5/1999 | Sholder et al. |
| 6,553,261 B2 | 4/2003 | Thong |
| 7,630,767 B1 | 12/2009 | Poore et al. |
| 8,457,742 B2 | 6/2013 | Jacobson |
| 8,521,278 B2 | 8/2013 | Shuros et al. |
| 8,532,785 B1 | 9/2013 | Crutchfield et al. |
| 8,761,879 B2 | 6/2014 | Hopper et al. |
| 8,948,832 B2 | 2/2015 | Hong et al. |

(Continued)

OTHER PUBLICATIONS (PCT/US2020/017851) PCT Notification of Transmittal of the International Search Report and the Written Opinion of the International Searching Authority, dated Jun. 29, 2020, 9 pages.

*Primary Examiner* — Brian T Gedeon

(57) ABSTRACT

An implantable medical device is configured determine a numerical value of a variable that is monitored by the implantable medical device and convert the numerical value to a data sequence of modulated electrical stimulation rate intervals. The implantable medical device delivers electrical stimulation pulses according to the data sequence of modulated stimulation rate intervals to cause a modulated rate of activation of excitable tissue of a patient corresponding to the modulated stimulation rate intervals. The modulated rate of activation is detectable by a rate monitor for demodulation to the numerical value of the monitored variable data value. In some examples, the implantable medical device is a pacemaker delivering cardiac pacing pulses according to modulated pacing rate intervals to cause a modulated heart rate of the patient detectable by a heart rate monitor for demodulation to the numerical value of the monitored variable.

28 Claims, 9 Drawing Sheets

(56) References Cited

U.S. PATENT DOCUMENTS

| | | |
|---|---|---|
| 9,572,503 B2 | 2/2017 | DeForest |
| 9,641,239 B2 | 5/2017 | Panther et al. |
| 9,669,224 B2 | 6/2017 | Carney et al. |
| 9,775,982 B2 | 10/2017 | Grubac et al. |
| 2012/0109236 A1 | 5/2012 | Jacobson et al. |
| 2013/0030494 A1 | 1/2013 | Meredith |
| 2014/0277245 A1 | 9/2014 | Lu et al. |
| 2016/0004224 A1 | 1/2016 | Pi |
| 2016/0121129 A1 | 5/2016 | Persson et al. |

ELECTRICAL STIMULATION RATE MODULATION FOR COMMUNICATION OF DATA VALUES IN A MEDICAL DEVICE SYSTEM

REFERENCE TO RELATED APPLICATION

This application claims the benefit of U.S. Patent Application No. 62/805,101 filed provisionally on Feb. 13, 2019, incorporated herein by reference in its entirety.

TECHNICAL FIELD

This disclosure relates to a medical device system including an implantable medical device (IMD) and method for modulating a rate of electrical stimulation pulses delivered by the IMD for communicating a numerical value of a monitored variable to another medical device.

BACKGROUND

A wide variety of implantable medical devices (IMDs) for delivering therapeutic electrical stimulation pulses to treat a medical condition have been used clinically or proposed for clinical use in patients. Examples include IMDs that deliver electrical stimulation therapy to the heart, muscle, nerve, brain, stomach or other tissue. Such IMDs employ electrodes for the delivery of therapeutic electrical signals to such organs or tissues. An IMD may include electrodes for sensing intrinsic physiological electrical signals within the patient, which may be propagated by such organs or tissue, and/or other sensors for sensing physiological signals of a patient. The electrodes used for delivering electrical stimulation pulses may be carried by a medical electrical lead extending from the IMD or carried on the housing of an IMD that encloses the electronic circuitry of the IMD.

For example, a leadless intracardiac pacemaker having housing-based electrodes may be implanted within a heart chamber for sensing cardiac electrical signals and delivering cardiac pacing pulses to detect and treat cardiac arrhythmias. A leadless intracardiac pacemaker may be miniaturized in order to facilitate implantation wholly within a single heart chamber. Other IMDs, such as neurostimulators for treating pain, incontinence, paralysis, tremor, or other neurological disorders or symptoms, may be miniaturized to reduce the complexity, invasiveness, or complications of an implantation procedure, reduce patient discomfort, or enable implantation in a limited anatomical space.

IMDs capable of delivering electrical stimulation therapy may be programmable devices capable of wireless communication with an external programming device, e.g., using radio-frequency (RF) telemetry. IMDs may transmit data about the therapy delivered, signals sensed from the patient or device diagnostic data to an external programming or monitoring device via the RF telemetry. In this way a clinician can adjust the therapy as needed or obtain additional information about the patient's condition or the IMD itself.

SUMMARY

The techniques of this disclosure generally relate to communicating a numerical value of a monitored variable through modulation of a rate of delivered electrical stimulation pulses by an IMD. An IMD operating according to the techniques disclosed herein determines a numerical value of a monitored variable and coverts the numerical value to a sequence of modulated stimulation rate intervals that represent the numerical value. A rate monitor detects the modulated rate of activation of excitable tissue caused by the modulated stimulation rate intervals and demodulates the detected rate to determine the numerical value of the monitored variable without requiring direct detection of the stimulation pulses by the rate monitor or radio frequency or other wirelessly transmitted signals to communicate the numerical value. In some examples, the 1 MB is a pacemaker delivering cardiac pacing pulses at modulated pacing rate intervals and the rate monitor is a heart rate monitor.

In one example, the disclosure provides a medical device system including an IMD having a control circuit configured to determine a numerical value of a variable that is monitored by the IMD according to a monitoring protocol and convert the numerical value to a data sequence of modulated stimulation rate intervals. The IMD includes a pulse generator configured to deliver electrical stimulation pulses according to the data sequence of the modulated stimulation rate intervals to cause a modulated rate of activation of an excitable tissue of a patient corresponding to the modulated stimulation rate intervals. The modulated rate of activation is detectable by a rate monitor for demodulation of the modulated rate of activation to the numerical value of the monitored variable value.

In another example, the disclosure provides a method including determining by an IMD a numerical value of a variable that is monitored by the 1 MB according to a monitoring protocol and converting the numerical value to a data sequence comprising a plurality of modulated stimulation rate intervals. The method further includes delivering electrical stimulation pulses by the IMD according to the data sequence of the modulated stimulation rate intervals to cause a modulated rate of activation by an excitable tissue of a patient corresponding to the modulated stimulation rate intervals. The modulated rate of activation is detectable by a rate monitor for demodulation of the modulated rate of activation to the numerical value of the monitored variable.

In yet another example, the disclosure provides a non-transitory, computer-readable storage medium comprising a set of instructions which, when executed by a control circuit of an IMD, cause the device to determine a numerical value of a variable that is monitored by the IMD according to a monitoring protocol and convert the numerical value to a data sequence of modulated stimulation rate intervals. The instructions further cause the IMD to deliver electrical stimulation pulses according to the data sequence of the modulated stimulation rate intervals to cause a modulated rate of activation of an excitable tissue a patient corresponding to the modulated stimulation rate intervals. The modulated rate of activation is detectable by a rate monitor for demodulation of the modulated rate of activation to the numerical value of the monitored variable.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
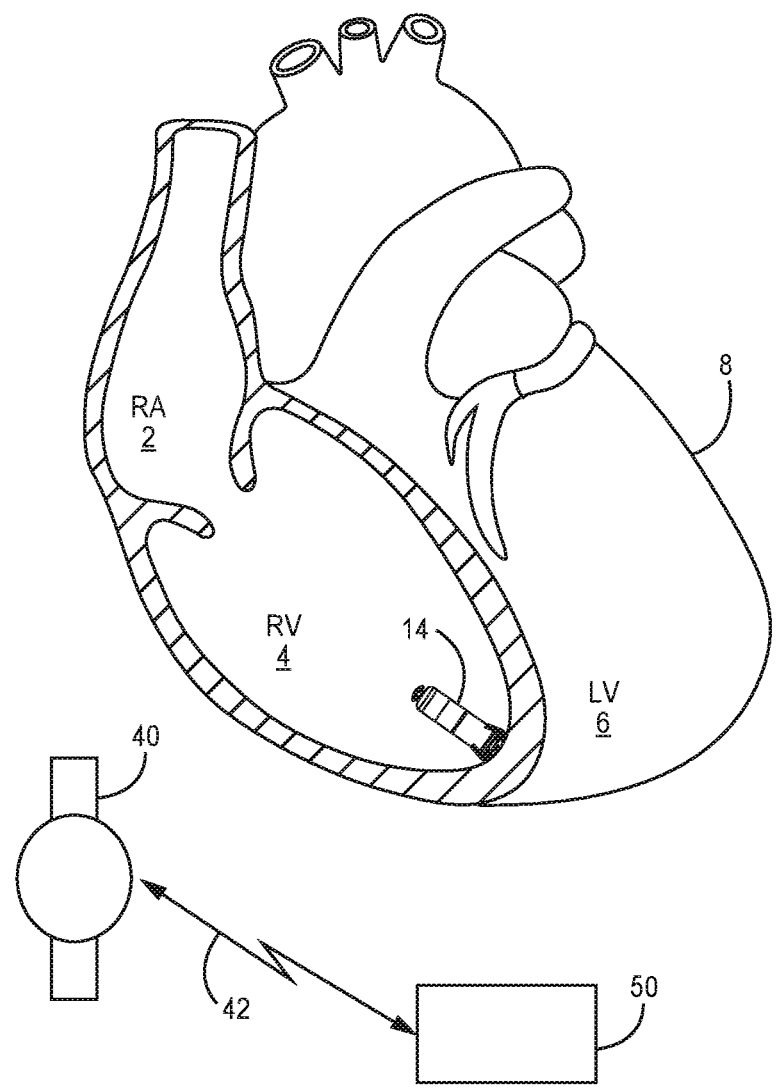
FIG. 1 is a conceptual diagram illustrating an IMD system that may be used to deliver therapeutic electrical stimulation pulses and modulate the rate of the stimulation pulses for communicating data to another device.

In general, this disclosure describes an IMD system configured to monitor device-and/or patient-related variables to determine a numerical value of a monitored variable and communicate the numerical value of the monitored variable by modulating rate intervals of electrical stimulation pulses delivered by the IMD. Each electrical stimulation pulse delivered at the modulated rate intervals is intended to cause capture or activation of an excitable tissue being stimulated. As used herein, the term "excitable tissue" refers to body tissue comprising cells that can generate an action potential at its membrane in response to depolarization and may transmit an impulse along the membrane. The term "activation" refers to an electrical depolarization or subsequent mechanical contraction caused by the electrical depolarization due to delivery of an electrical stimulation pulse by the IMD. Examples of excitable tissue include skeletal muscle, smooth muscle, cardiac muscle, nerves, spinal cord and brain. A rate monitor detects the rate of depolarization or contraction of the excitable tissue caused by the modulated rate of stimulation pulses by detecting a physiological signal comprising waveforms occurring at the rate of depolarization or contraction of the excitable tissue. The rate monitor thereby detects modulated rates of activations of the excitable tissue from the physiological signal and demodulates the detected rates to determine the numerical value of the monitored variable.

In some examples of the techniques disclosed herein, the 1 MB is a pacemaker, cardioverter/defibrillator or other IMD capable of generating and delivering the electrical stimulation pulses as cardiac pacing pulses intended to capture the myocardium or nerves of the heart. The cardiac pacing pulses are delivered at modulated cardiac pacing rate intervals to cause depolarization and subsequent mechanical contraction of the heart at the modulated rate intervals. A heart rate monitor can detect the resulting modulated heart rate and demodulated detected heart rates to determine the numerical value of a patient-related or device-related variable monitored by the IMD.

This data communication technique including modulating the rate of electrical stimulation pulses delivered by the IMD does not require the IMD to communicate the numerical value using a radio frequency (RF) transceiver or other dedicated circuitry used for transmitting wireless communication signals. Further, the rate monitor is not required to detect the electrical stimulation pulses delivered by the IMD. The rate monitor detects a rate of activation, e.g., the electrical depolarization or the resulting mechanical contraction, of the stimulated tissue without detecting the actual stimulation pulses or any specific feature of the stimulation pulses themselves. For instance, the rate monitor may detect a heart rate from a physiological sensor signal for demodulating a modulated rate of cardiac pacing pulses without detecting the cardiac pacing pulses themselves.

As used herein, a "monitored variable" is a patient- or device-related variable that is monitored or measured by the IMD and is not set or directly controlled by the IMD, the rate monitor or any other device as a control parameter for controlling a function of the IMD or rate monitor. For example, monitored variables may include remaining battery voltage of the IMD, cardiac pacing capture threshold, electrical impedance of a cardiac pacing vector, or the resulting frequency of cardiac pacing out of a total number of sensed cardiac and paced cardiac events over a specified time period as examples. A monitored variable is not directly set or controlled by the IMD in contrast to a control parameter that is programmed or automatically set by the 1 MB to control IMD functions.

A "control parameter" as used herein is a parameter that is programmed into or set or adjusted by the IMD to control 1 MB sensing and therapy delivery functions. A sensing control parameter, for example, is used to control the sensing of physiological signals, e.g., sensing of cardiac electrical signals such as R-waves or P-waves. Examples of sensing control parameters may include, with no limitation intended, a sensing threshold, sensitivity, blanking period, and refractory period. While these control parameters are used to control how the IMD senses events from a physiological signal, the number of sensed events, e.g., the number of sensed R-waves may be a monitored or measured variable that is not directly set by the IMD. Examples of therapy delivery or electrical stimulation control parameters may include, with no limitation intended, pacing lower rate, pacing pulse amplitude, and pacing pulse width. These parameters are directly programmed into, set or adjusted by the IMD. The capture threshold used to set the pacing pulse amplitude, however, is an example of a monitored variable that has a numerical value and is not set or controlled by the IMD. The pacing rate modulation techniques disclosed herein are used for communicating a numerical value of a monitored variable.

A "physiological signal" as used herein is a signal that is produced by sensor, e.g., an electrical, chemical, mechanical or optical sensor of the IMD or rate monitor, in response to a physiological change in a body tissue. A physiological signal as used herein does not refer to a signal such as an electrical stimulation pulse that is produced by a device and detected by another device. One example of a physiological signal is a cardiac electrical signal that is produced by a cardiac electrical sensing circuit from signals received by sensing electrodes and includes depolarization signals attendant to the electrical depolarization of myocardial tissue. Other examples of physiological signals, with no limitation intended, include pulsatile signals that can be sensed by mechanical or optical sensors and include pulsatile signals produced by cyclical changes in blood volume corresponding to the cardiac cycle or cyclical changes in motion of the heart chambers or blood vessel walls. In the communication techniques disclosed herein, the rate monitor senses a physiological signal and determines activation rates corresponding to modulated rate intervals of electrical stimulation pulses delivered by the IMD. In the examples presented herein, the rate monitor does not directly detect the electrical stimulation pulses delivered by the IMD or demodulate the characteristics or features of the actual stimulation pulses delivered by the IMD. The rate monitor detects the rate of activations, e.g., electrical depolarizations or mechanical contractions, represented by pulsatile or cyclical waveforms of a physiological signal sensed by a sensor of the rate monitor.

FIG. 1 is a conceptual diagram illustrating an IMD system 10 that may be used to deliver therapeutic electrical stimulation pulses and modulate the rate of the stimulation pulses for communicating data to another device. In the illustrative example of FIG. 1, system 10 includes an IMD shown as an intracardiac pacemaker 14 and an external, wearable heart rate monitor (HRM) 40. Pacemaker 14 is configured to deliver therapeutic pacing pulses to heart 8 to treat or prevent arrhythmias. Pacemaker 14 is configured to modulate pacing rate intervals to deliver pacing pulses at different rates in accordance with an encoding scheme. As described herein the encoding scheme may be based on a binary, ternary, quaternary or other base number system or other encoding scheme that includes predetermined pacing rate intervals used to cause the heart to beat at modulated heart rates. The HRM 40 detects the modulated heart rates and demodulates the heart rates to a numerical value of a variable monitored by the pacemaker 14.

As used herein, "therapeutic" pacing pulses includes pacing pulses intended to capture the heart 8 to cause a pacing-evoked myocardial depolarization to cause the heart to contract or "beat" at an intended rate. As examples, pacemaker 14 may deliver bradycardia pacing therapy by delivering therapeutic pacing pulses at a programmed lower pacing rate in the absence of intrinsic R-waves being sensed at or above the programmed lower pacing rate. Rate responsive pacing therapy may include therapeutic pacing pulses delivered at a temporary pacing rate above the programmed lower pacing rate to increase the heart rate during physical activity. As disclosed herein, each pacing pulse delivered at a modulated pacing rate interval may be considered a "therapeutic" pacing pulse in that it is delivered outside the physiological refractory period of the myocardial tissue at a pacing pulse energy intended to capture the heart and cause a heartbeat above a programmed lower pacing rate thereby preventing asystole or bradycardia.

The pacing pulses delivered at modulated pacing rate intervals (also referred to herein as "modulated pacing intervals") may be delivered without suspending bradycardia pacing in a pacing dependent patient, for instance, in that pacing pulses delivered at the modulated pulse intervals capture the heart at a rate interval within an acceptable range of a programmed lower pacing rate or other targeted therapeutic pacing rate or a sensed intrinsic heart rate. For example, if the programmed lower rate for bradycardia pacing is 40 to 60 pulses per minute, corresponding to a pulse rate interval of 1.5 to 1.0 seconds, modulated pacing rate intervals for communicating a numerical value of a monitored variable may be in the range of about 1000 ms to about 660 ms corresponding to overdrive pacing rates of about 60 to about 90 pulses per minute, as examples with no limitation intended. Since the number of modulated pacing rate intervals required to communicate one or more numerical values of one or more monitored variables can generally be delivered within a few minutes or even one minute or less, the modulated pacing rates can be delivered without compromising the intended therapeutic benefit of a pacing therapy such as bradycardia pacing. For example, modulated pacing rates may account for about 1% or even 0.1% or less of the total number of pacing pulses delivered by pacemaker 14 over 24 hours.

In the example of FIG. 1, pacemaker 14 is shown in the right ventricle (RV) of the patient's heart 8 for sensing cardiac electrical signals and delivering cardiac pacing pulses. Pacemaker 14 may be a transcatheter intracardiac pacemaker adapted for implantation wholly within a heart chamber, e.g., wholly within the RV 4, wholly within the left ventricle (LV) 6, or wholly with the right atrium (RA) 2. Pacemaker 14 may be reduced in size compared to subcutaneously implanted pacemakers and may be generally cylindrical in shape to enable transvenous implantation in a heart chamber via a delivery catheter.

The techniques disclosed herein are not limited to the pacemaker location shown in the example of FIG. 1 and other positions within heart 8 are possible. For example, a pacemaker 14 performing the techniques disclosed herein may be positioned at other locations in or on the heart 8 for delivering electrical stimulation pulses that capture and pace the heart at the rate of the electrical stimulation pulses. Pacemaker 14 may deliver the cardiac pacing pulses via electrodes on the outer housing of the pacemaker, referred to herein as "housing based electrodes." Pacemaker 14 may be configured to sense a cardiac electrical signal from the RV 4 using the housing based electrodes for detecting ventricular R-waves for producing a ventricular electrogram (EGM) signal. The cardiac electrical signals may be sensed using the housing based electrodes that are also used to deliver pacing pulses to the heart 8.

HRM 40 may be a wearable device that is capable of detecting the patient's heart rate and demodulate the heart rate to extract information communicated from pacemaker 14. HRM 40 may be a dedicated heart rate tracking device provided to the patient receiving pacemaker 14 for detecting and demodulating modulated heart rates for obtaining numerical values of variables monitored by pacemaker 14. In other examples, HRM 40 may be a commercially available smart watch, activity tracker, or other wearable accessory capable of detecting the patient's heart rate and storing and executing an application for demodulating the detected heart rate to extract data encoded in the modulated heart rate. In still other examples, HRM 40 may be an implantable device, e.g., a device that is implantable for sensing a subcutaneous ECG signal such as the Reveal LINQ® Insertable Cardiac Monitoring System available from Medtronic, Inc., Minneapolis Minn. As described below, HRM 40 may detect a modulated heart rate and demodulate the heart rate to determine a numerical value of one or more patient-related and/or device-related variables monitored by pacemaker 14. HRM 40 may provide a variety of responses to a numerical value of a monitored variable such as generating a patient notification that data is available for viewing, generating an alert that a numerical value is outside a normal range, generating a display of the numerical value which may include historic values of the monitored variable, generating a notification of the status of the monitored variable based on the numerical value, and/or transmitting the numerical value to another device.

HRM 40 may be capable of bidirectional wireless communication with an external device 50 for transmitting data demodulated from the detected heart rate to external device 50. External device 50 may be a home medical monitor, a smart phone or other hand held device, a personal computer or other device that may be used by the ambulatory patient or at a fixed location in the patient's home or other location for wirelessly retrieving data from HRM 40. External device 50 is shown with a wireless communication link 42 established with HRM 40. Communication link 42 may be established using a radio frequency (RF) link such as BLUETOOTH®, Wi-Fi, Medical Implant Communication Service (MICS) or other communication bandwidth. In some examples, HRM 40 and external device 50 are BLUETOOTH® enabled devices to allow data extracted from the detected heart rates by HRM 40 to be transmitted to external device 50 or cloud-based storage any time a BLUETOOTH® connection is available. External device 50 may be a MYCARELINK™ Patient Monitor available from Medtronic, Inc. Minneapolis Minn., USA, in one example.

HRM 40 and/or external device 50 may display numerical values or a status indicator of the numerical value demodulated from the detected heart rate to the patient or other user to view, enabling the patient or other user to take any corrective action as needed. Notifications or alerts may be initiated by the HRM 40 for display to the patient directly or via the external device 50. Accessibility to patient-related or device-related variables that are monitored or measured by pacemaker 14 is provided without requiring pacemaker 14 to perform wireless radio frequency transmission. The operation of pacemaker 14 for communicating data to a patient or clinician via an external device is improved by making the communication process power efficient (powering of an RF transmitter is not required). Numerical values of monitored parameters can be made available from pacemaker 14 multiple times throughout an hour, day, week, etc., when HRM 40 is detecting the patient's heart rate. Patient alerts or notifications can be initiated by HRM without time constraint or waiting for an interrogation command from another device. Data may be obtained from pacemaker 14 with a higher compliance rate when data is communicated without reliance on patient or user interaction with system 10, e.g., by manually initiating a communication session.

It is contemplated that HRM and/or external device 50 may be in wired or wireless connection to a communications network via a telemetry circuit that includes a transceiver and antenna or via a hardwired communication line for transferring data to a centralized database or computer to allow remote management of the patient. Remote patient management systems including a remote patient database may be configured to receive data and information determined by HRM 40 to enable a clinician to review data communicated through heart rate modulation by pacemaker 14.

While a pacemaker 14 and wearable HRM 40 are shown in system 10, it is contemplated that other types of implantable electrical stimulation devices may deliver therapeutic individual pulses or individual pulse trains, e.g., high frequency pulse trains for muscle stimulation or pain control, separated by rate intervals. The implantable electrical stimulation device may be configured to determine a monitored variable data value relating to a patient or device condition and convert the numerical data value to a sequence of modulated rate intervals (between individual stimulation pulses or between high frequency trains of pulses). A rate monitor, which may be a wearable or implantable monitor, may be configured to detect a signal including the resulting evoked responses or activations of the stimulated muscle or nerve tissue occurring at the modulated rate. The rate detecting device may determine the rate of evoked responses or activations, e.g., from a neural signal, electromyogram signal or mechanical sensor signal, and demodulate the rate to determine a numerical value of a device-related or patient-related variable. The HRM 40 monitor may be configured only for monitoring in some examples but may include therapy delivery capabilities in other examples. For instance, the HRM configured to demodulate a detected heart rate may be a pacemaker, implantable cardioverter defibrillator, neurostimulator, or other medical device capable of both detecting a rate of activations produced by the modulated stimulation rate of the IMD and delivering a therapy, such as an electrical stimulation therapy, drug delivery or other therapy.

Figure 2:
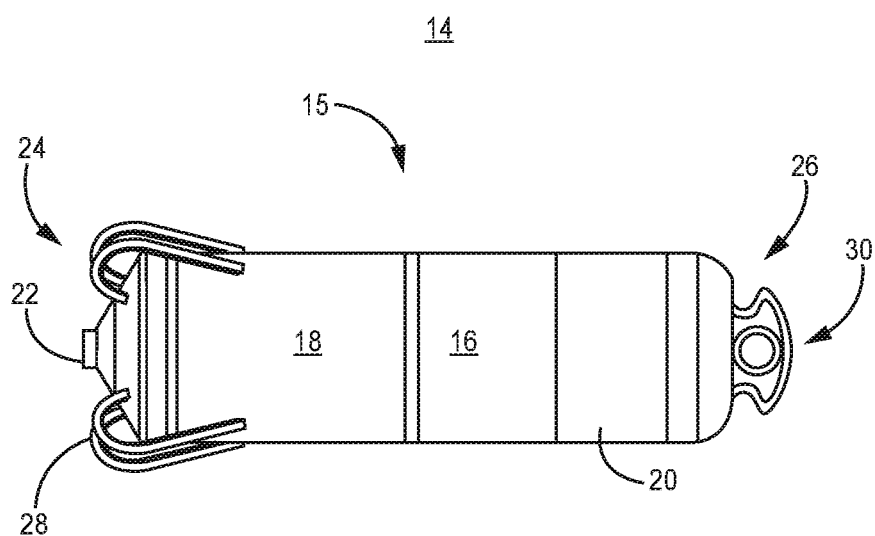
FIG. 2 is a conceptual diagram of the intracardiac pacemaker shown in FIG. 1.

FIG. 2 is a conceptual diagram of the intracardiac pacemaker 14 shown in FIG. 1. Pacemaker 14 includes leadless electrodes 20 and 22 spaced apart on the housing 15 of pacemaker 14 for sensing cardiac electrical signals and delivering pacing pulses. Electrode 22 is shown as a tip electrode extending from a distal end 24 of pacemaker 14, and electrode 20 is shown as a ring electrode along a mid-portion of the lateral wall of housing 15, for example adjacent proximal end 26. Electrode 20 may circumscribe a portion of the lateral sidewall of housing 15 that extends from distal end 24 to proximal end 26. Distal end 24 is referred to as "distal" in that it is expected to be the leading end as pacemaker 14 is advanced through a delivery tool, such as a catheter, and placed against a targeted pacing site.

Electrodes 20 and 22 form an anode and cathode pair for bipolar cardiac pacing and cardiac electrical signal sensing. In alternative embodiments, pacemaker 14 may include two or more ring electrodes, two tip electrodes, and/or other types of electrodes exposed along pacemaker housing 15 for delivering electrical stimulation to heart 8 and sensing cardiac electrical signals. Electrodes 20 and 22 may be positioned at locations along pacemaker 14 other than the locations shown. Electrodes 20 and 22 may be, without limitation, titanium, platinum, iridium or alloys thereof and may include a low polarizing coating, such as titanium nitride, iridium oxide, ruthenium oxide, platinum black among others.

Housing 15 is formed from a biocompatible material, such as a stainless steel or titanium alloy. In some examples, the housing 15 may include an insulating coating. Examples of insulating coatings include parylene, urethane, PEEK, or polyimide among others. The entirety of the housing 15 may be insulated, but only electrodes 20 and 22 uninsulated. Electrode 22 may serve as a cathode electrode and be coupled to internal circuitry, e.g., a pacing pulse generator and cardiac electrical signal sensing circuitry, enclosed by housing 15 via an electrical feedthrough crossing housing 15. Electrode 20 may be formed as a conductive portion of housing 15 defining a ring electrode that is electrically isolated from the other portions of the housing 150 as generally shown in FIG. 2. In other examples, the entire periphery of the housing 15 may function as an electrode that is electrically isolated from tip electrode 22, instead of providing a localized ring electrode such as anode electrode 20. Electrode 20 defined by an electrically conductive portion of housing 15 serves as a return anode during pacing and sensing.

The housing 15 includes a control electronics subassembly 18, which houses the electronics for sensing cardiac signals, producing pacing pulses and controlling therapy delivery and other functions of pacemaker 14 as described below in conjunction with FIG. 3. Housing 15 further includes a battery subassembly 16, which provides power to the control electronics subassembly 18.

Pacemaker 14 may include a set of fixation tines 28 to secure pacemaker 14 to patient tissue, e.g., by actively engaging with the ventricular endocardium and/or interacting with the ventricular trabeculae. Fixation tines 28 are configured to anchor pacemaker 14 to position electrode 22 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned U.S. Pat. No. 9,775,982 (Grubac, et al.), hereby incorporated herein by reference in its entirety.

Pacemaker 14 may optionally include a delivery tool interface 30. Delivery tool interface 30 may be located at the proximal end 26 of pacemaker 14 and is configured to connect to a delivery device, such as a catheter, used to position pacemaker 14 at an implant location during an implantation procedure, for example within the LV.

Figure 3:
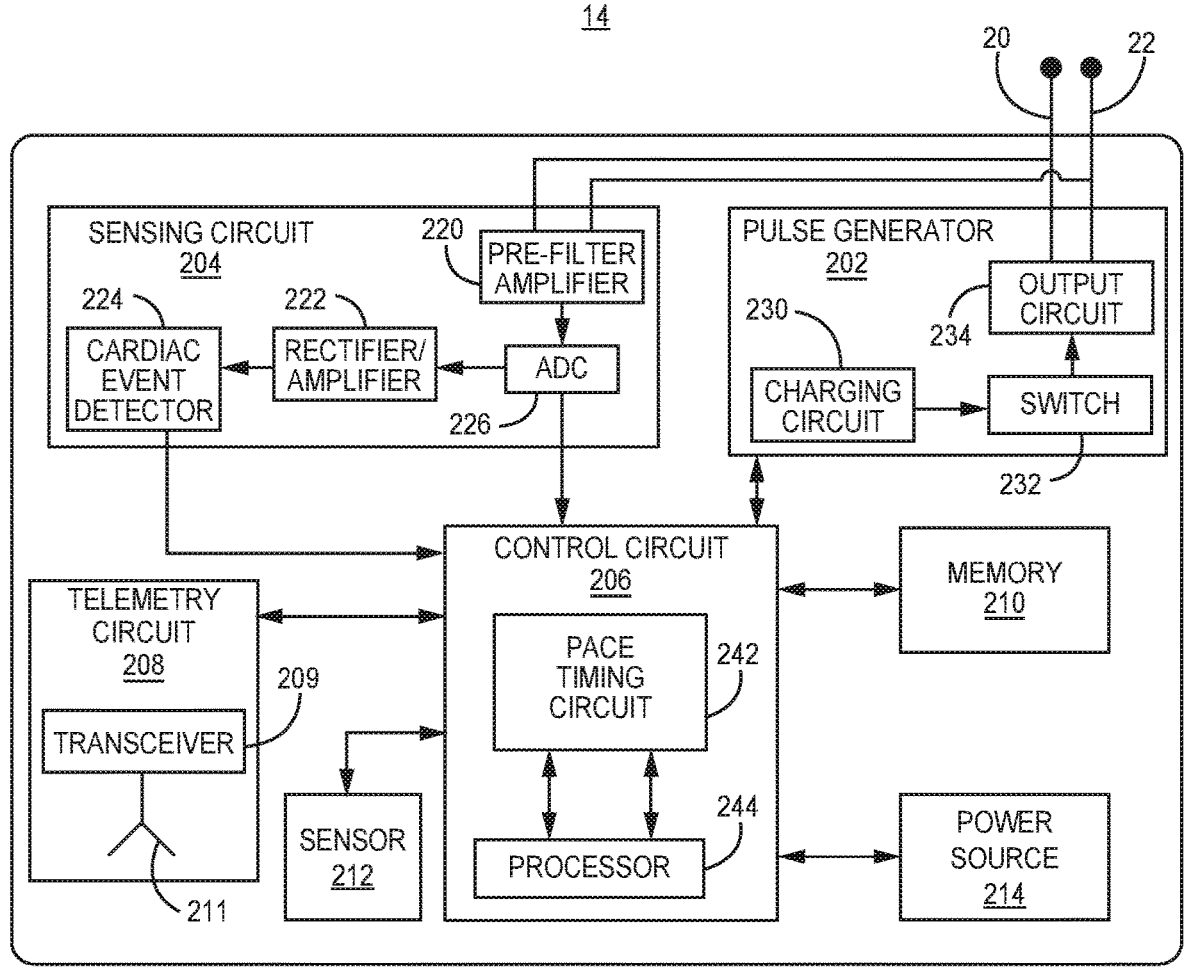
FIG. 3 is a schematic diagram of an example configuration of the pacemaker shown in FIG. 2.

FIG. 3 is a schematic diagram of an example configuration of pacemaker 14 shown in FIG. 1. Pacemaker 14 includes a pulse generator 202, a cardiac electrical signal sensing circuit 204 (also referred to herein as "sensing circuit 204"), a control circuit 206, memory 210, telemetry circuit 208 and a power source 214. The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Cardiac electrical signal sensing circuit 204 is configured to receive a cardiac electrical signal via electrodes 20 and 22 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital convertor (ADC) 226. ADC 226 may pass a multi-bit, digital electrogram (EGM) signal to control circuit 206 for use in detecting cardiac events and determining a patient's heart rhythm. The digital signal from ADC 226 may be passed to rectifier and amplifier circuit 222, which may include a rectifier, bandpass filter, and amplifier for passing the filtered and rectified cardiac electrical signal to cardiac event detector 224.

Cardiac event detector 224 may include a sense amplifier or other detection circuitry that compares the incoming rectified, cardiac electrical signal to an R-wave detection threshold amplitude, which may be an auto-adjusting threshold. When the incoming signal crosses the R-wave detection threshold, the cardiac event detector 224 produces an R-wave sensed event signal that is passed to control circuit 206. R-wave sensed event signals passed from cardiac event detector 224 to control circuit 206 may be used for scheduling ventricular pacing pulses by pace timing circuit 242, determining ventricular rate intervals or RR intervals (between two consecutively received R-wave sensed event signals. Control circuit 206 may determine an intrinsic heart rate from the RR intervals.

Control circuit 206 includes pace timing circuit 242 and processor 244. Control circuit 206 may receive R-wave sensed event signals and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses. Pace timing circuit 242 (or processor 244) may receive R-wave sensed event signals from cardiac event detector 224 for use in controlling the timing of pacing pulses delivered by pulse generator 202 and determining an intrinsic heart rate when pacemaker 14 is not delivering pacing pulses.

Control circuit 206 may retrieve programmable pacing control parameters, such as pacing pulse amplitude and pacing pulse width, which are passed to pulse generator 202 for controlling pacing pulse delivery from memory 210. In addition to providing control signals to pace timing circuit 242 and pulse generator 202 for controlling pacing pulse delivery, control circuit 206 may provide sensing control signals to sensing circuit 204 (e.g., R-wave sensing threshold, sensitivity, and/or various blanking and refractory intervals applied to the cardiac electrical signal).

Pulse generator 202 generates electrical pacing pulses that are delivered to the RV of the patient's heart via cathode electrode 22 and return anode electrode 20. Pulse generator 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of a pacing interval and kept closed for a programmed pacing pulse width to enable discharging of the holding capacitor of charging circuit 230. The holding capacitor, previously charged to the pacing pulse voltage amplitude, is discharged across electrodes 20 and 22 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 for generating and delivering a pacing pulse.

Pacemaker 14 may include a sensor 212 for producing a physiological signal used by control circuit 206 for monitoring a patient-related variable. For example, sensor 212 may include a motion sensor such as an accelerometer for detecting motion of the heart and/or motion caused by patient physical activity. Additionally or alternatively, sensor 212 may include a pressure sensor, optical sensor, acoustical sensor, temperature sensor, pH sensor, or any combination thereof. Control circuit 206 may derive a numerical value of a patient condition from a signal received from sensor 212 according to a monitoring protocol.

Control circuit 206 is configured to monitor one or more patient-related and/or device related variables. Among the variables that may be monitored by control circuit 206 are battery voltage of power source 214, pacing electrode impedance, pacing capture threshold determined by performing a pacing capture threshold test, percentage of pacing pulses delivered out of all paced and sensed events, number of premature ventricular contractions (PVC) or runs of PVCs detected, number of atrial arrhythmia episodes or atrial arrhythmia burden, percentage of time pacing at a rate response rate, percentage of time pacing at a programmed lower rate, percentage of time at a resting physical activity level, blood oxygen saturation, or blood pressure as examples. Control circuit 206 may monitor a variable by detecting or determining a numerical value of the variable according to a predetermined schedule or protocol stored in memory 210. The numerical value of a monitored device-related variable may be determined by circuitry included in pacemaker 14, e.g., for measuring voltage of a battery included in power source 214. The numerical value of a monitored patient-related variable may be determined using a signal from sensor 212 or cardiac electrical signal sensing circuit 204, e.g., for determining blood oxygen saturation, blood pressure, cardiac impedance, pacing capture threshold or other patient related variables. It is recognized that numerous types of variables may be monitored by pacemaker 14 on a weekly, daily, hourly, or more or less frequent basis or on a triggered basis. The methods for communicating a numerical value of a monitored variable by pacing rate interval modulation disclosed herein are not limited any specific type of monitored variables.

Control circuit 206 is configured to convert the numerical value of a monitored variable to a data sequence of modulated pacing rate intervals. The modulated pacing rate intervals may correspond to a binary sequence of zeros and ones in some examples. For instance, a binary representation of the monitored variable numerical value may be converted to a modulated pacing rate interval data sequence by converting all zeros in the binary representation of the numerical variable value to a first pacing interval and converting all ones in the sequence to a second, different pacing interval. For example, for each zero in the sequence, a pacing pulse interval may be set to 700 ms. For each one in the sequence, a pacing pulse interval may be set to 800 ms. When a ternary encoding scheme is used, three pulse intervals, e.g., 700, 750 and 800 ms may be used. Four pulse intervals, e.g., 700, 750, 800 and 800 ms intervals, may be used in converting a numeric value of a monitored variable to a sequence of pacing intervals representing a quaternary value and so on. When a higher base number system is used to convert a variable numerical value to modulated pacing intervals, fewer modulated pacing intervals may be required to encode the numerical value in a sequence of modulated pacing intervals. For example, a quaternary encoding scheme may require half the number of modulated pacing intervals to encode a numerical value of a monitored variable than a binary encoding scheme.

In other examples, control circuit 206 converts the numerical value of a monitored variable to modulated pacing rate intervals by setting the modulated pacing rate interval to a fixed pacing interval for a number of intervals equal to a digit of the numerical value. For example, if a digit of the numerical value is a 6, the pacing rate interval is set to a fixed rate interval for 6 pacing cycles to communicate the numerical value of a "6." Multiple sets of pacing rate intervals may be delivered for communicating a multi-digit numerical value where each set has a number of pacing rate intervals equal to the value of one digit of the multi-digit numerical value.

Control circuit 206 establishes a sequence of modulated pacing rate intervals representing the numerical value of a monitored variable by controlling pace timing circuit 242 to set timers or control signals according to the modulated pacing rate intervals. Pulse generator 206 responds to signals received from pace timing circuit 242 by generating and delivering therapeutic pacing pulses, e.g., having a pacing pulse amplitude and pulse width that captures the myocardial tissue to cause a pacing evoked depolarization, according to the modulated pacing rate interval sequence. In various examples, the modulated pacing rate interval sequence may include a header including one or more pacing pulses delivered at interval(s) that signal that subsequent pulses are being delivered at modulated pulse intervals for communicating one or more monitored data values. The modulated pacing rate interval sequence may be repeated one or more times to increase the likelihood of successful detection and demodulation of the modulated heart rate by the HRM 40. Other examples of sequences of modulated pacing rate intervals and associated techniques are described below.

Memory 210 may include computer-readable instructions that, when executed by processor 244 of control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media. Memory 210 may store timing intervals and other data used by control circuit 206 to control the delivery of pacing pulses by pulse generator 202 according to the techniques disclosed herein.

Power source 214 may correspond to battery subassembly 16 shown in FIG. 2 and provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 3 for the sake of clarity but are to be understood from the general block diagram of FIG. 3. For example power source 214 may provide power to charging circuit 230 for charging a holding capacitor to a pacing voltage amplitude, current to switch 232 and other circuitry included in pulse generator 202 as needed to generate and deliver pacing pulses. Power source 214 also provides power to telemetry circuit 208, sensing circuit 204 and sensor 212 as needed as well as memory 210.

Pacemaker 14 may optionally have a telemetry circuit 208 including a transceiver 209 and antenna 211 for transferring and receiving data, e.g., via a radio frequency (RF) communication link with an external programmer or home monitor. Telemetry circuit 208 may be used to transmit larger amounts of data and for receiving programming commands for setting programmable pacing and cardiac sensing parameters, for example. Telemetry circuit 208 may be capable of bi-directional communication with external device 50 (FIG. 1), for example, when external device 50 is a programmer or home monitor used to transmit programming commands to pacemaker 14 and retrieve data from pacemaker 14. Cardiac electrical signals, marker channel data depicting the timing of cardiac event sensing and pacing, currently programmed parameters or other data may be transmitted by telemetry circuit 208 to external device 50. Programmable control parameters and programming commands for controlling cardiac electrical signal sensing and cardiac pacing may be received by telemetry circuit 208 and stored in memory 210 for access by control circuit 206.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, pacing rate modulation operations performed by pacemaker 14 may be implemented in control circuit 206 executing instructions stored in memory 210 for controlling pulse generator 202.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern IMD, given the disclosure herein, is within the abilities of one of skill in the art. The functionality and components described in conjunction with FIG. 3 for performing cardiac pacing rate modulation for communicating a value of a monitored variable may generally be included in any 1 MB or wearable medical device configured to deliver electrical stimulation therapy to cause depolarization or activation of excitable tissue at a modulated rate.

Figure 4:
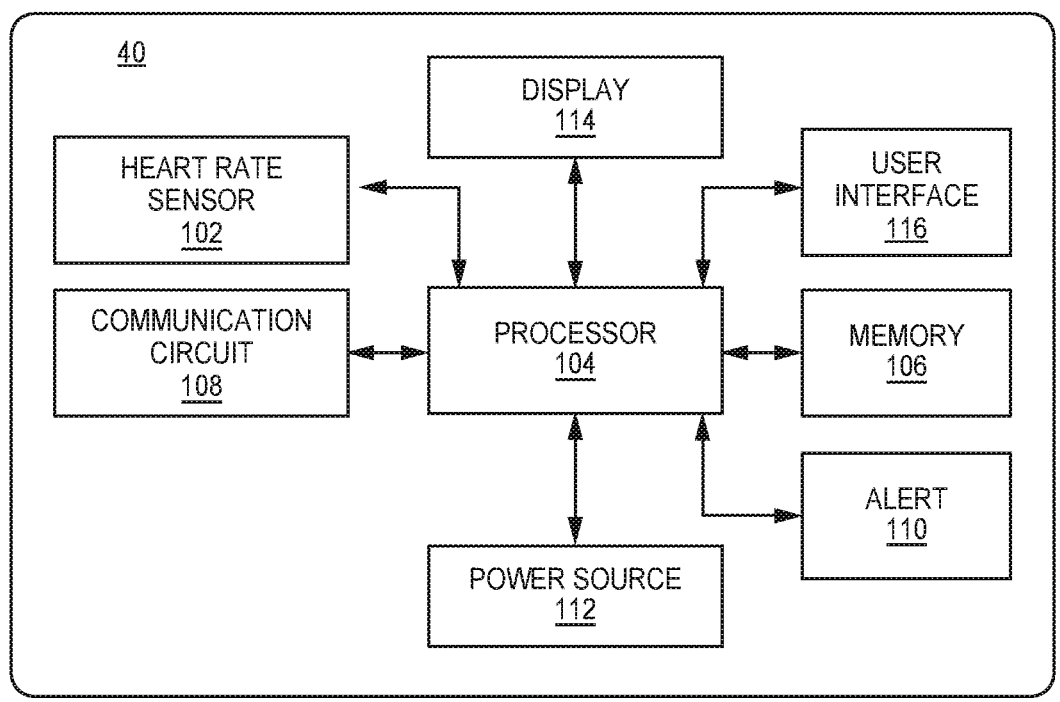
FIG. 4 is a conceptual diagram of the heart rate monitor (HRM) of FIG. 1.

FIG. 4 is a conceptual diagram of the HRM 40 of FIG. 1 according to one example. HRM 40 may take a variety of forms but is generally an implantable or wearable device equipped with a sensor for producing a pulsatile signal having a frequency correlated to heart rate and a processor for detecting heart rate from the signal and demodulating the detected heart rate to a numerical value of a variable monitored by pacemaker 14. HRM 40 is shown as a smart watch in the example of FIG. 1 but may be configured as a wearable band, strap or patch, such as a chest strap, arm or wrist band, head band or other wearable device such as earbuds. HRM 40 may include a heart rate sensor 102, processor 104, memory 106, communication circuit 108, alert circuit 110, power source 112, display 114 and user interface 116. In other examples, HRM 40 may be a subcutaneously implantable device that does not include a display 114 and user interface 116 but is capable of monitoring heart rate and transmitting data values demodulated from the heart rate via communication circuit 108 via BLUETOOTH® or other RF wireless communication. As indicated previously, an example of an implantable HRM that may be included in the disclosed system is the Reveal LINQ® Insertable Cardiac Monitor available from Medtronic, Inc., Minneapolis Minn. In still other examples, the HRM may be an implantable or wearable medical device having therapy delivery capabilities in addition to the capability of detecting a rate of depolarizations or contractions produced by electrical stimulation pulses generated and delivered by another medical device. Such devices may include pacemakers, implantable cardioverter defibrillators, neurostimulators, drug delivery pumps, or the like. While a therapy delivery circuit or module is not shown in FIG. 4, it is to be understood that the functions attributed to HRM 40 may be included in a medical device having additional components than those shown in FIG. 4, which may include circuitry and components for generating or delivering a therapy.

Power source 112 provides power to processor 104, heart rate sensor 102 and the other circuits of HRM 40 as needed. Power source 112 may include one or more rechargeable or non-rechargeable batteries. Heart rate sensor 102 may include electrodes for receiving electrical signals produced by the patient's heart and circuitry for sensing R-waves attendant to ventricular depolarizations for detecting heart beats. In other examples, heart rate sensor 102 includes an optical sensor and circuitry for determining heart rate using photoplethysmography (PPG), a bioimpedance sensor for detecting heart rate from cyclical tissue impedance changes, or another sensor capable of producing a pulsatile signal correlated to the patient's heart rate.

Processor 104 determines the patient's heart rate from a signal received from heart rate sensor 102. Processor 104 may determine the heart rate by detecting and counting individual pulses of the pulsatile signal over a predetermined or variable time interval, timing the intervals between consecutive individual pulses of the pulsatile signal, performing fast Fourier transform (FFT) over a predetermined time interval for determining the frequency of the pulsatile signal, or other technique for detecting the patient's heart rate from the heart rate sensor signal. Processor 104 may execute instructions stored in memory 106 for determining heart rate and for demodulating heart rate intervals for determining a numerical value of a monitored, variable data value that is communicated from pacemaker 14 via heart rate modulation. HRM 40 may be configured to monitor the user's heart rate continuously, at specified times of day, at regularly scheduled time intervals, or according to a predetermined monitoring protocol, which may be customizable for a given patient. An application may be stored in memory 106 for execution by processor 104 each time the heart rate is determined to detect one or more heart rate intervals that are known to be included in the encoding scheme for establishing a sequence of modulated pacing rate intervals.

Processor 104 may determine one or more numerical values corresponding to a respective number of monitored variables by demodulating heart rate intervals and may display a notification to the user on display 114 to notify the user that new data is available for viewing. In some examples, processor 104 may transmit the determined numerical values to another device, such as external device 50 or another implantable or wearable medical device, via communication circuit 108. Communication circuit 108 includes a wireless transceiver for transmitting and receiving radio frequency signals. For example, communication circuit 108 may be a BLUETOOTH® enabled device for transmitting and receiving data from external device 50. In this way, numerical values of device-related and/or patient-related variables may be communicated to HRM 40 by pacemaker 14 using only modulated pacing rate intervals without requiring wireless radio frequency communication transmission by pacemaker 14 and the associated power consumption and without disruption of cardiac pacing.

In some examples, processor 104 may compare a determined numerical data value to a threshold value or range and generate an alert or notification by alert circuit 110 to notify the user of the corresponding status of the monitored variable, e.g., as being within a normal or outside a normal range. The user may be alerted when a monitored variable value is outside a normal range and may be advised to contact his/her physician or seek medical attention. Alert circuit 110 may generate a vibration or audible tone to alert the user, and/or a visual display may be generated by display 114 notifying the user that the numerical data value determined from the modulated heart rate intervals is out of a normal range. In other examples, the alert generated based on the numerical data value may be an indication that the pacemaker 14 (or other IMD performing the electrical stimulation rate modulation) is changing a therapy delivery mode, stopping therapy delivery, performing a temporary operation or other status indicator. The alert may be transmitted to another medical device, which may respond to the alert by notifying a clinician or altering its own therapy delivery and/or monitoring functions in the medical device system 10.

HRM 40 may include a user interface 116 which may include a touch screen, buttons, voice response, or other interface or combinations thereof that enable the user to set user-selectable settings that control notifications and alerts or other functions of HRM 40. User interface 116 and display 114 may be configured to enable a user to select monitored variables and display current and/or historic numerical values of a monitored variable in a tabular or graphical format. For example, a user may select to be notified by HRM 40 each time new data is available, once a day or other selected frequency. In other examples, a user may select to be notified by HRM 40 only when a numeric value is outside a normal range. At other times, a user may select to disable patient notifications relating data values derived from the modulated heart rate and only enable transmission of numerical values of monitored variables to another medical device, e.g., to external device 50, to another implantable or wearable therapy delivery device, to a clinician's computer, phone or other device, or to a central patient management database, etc.

Figure 5:
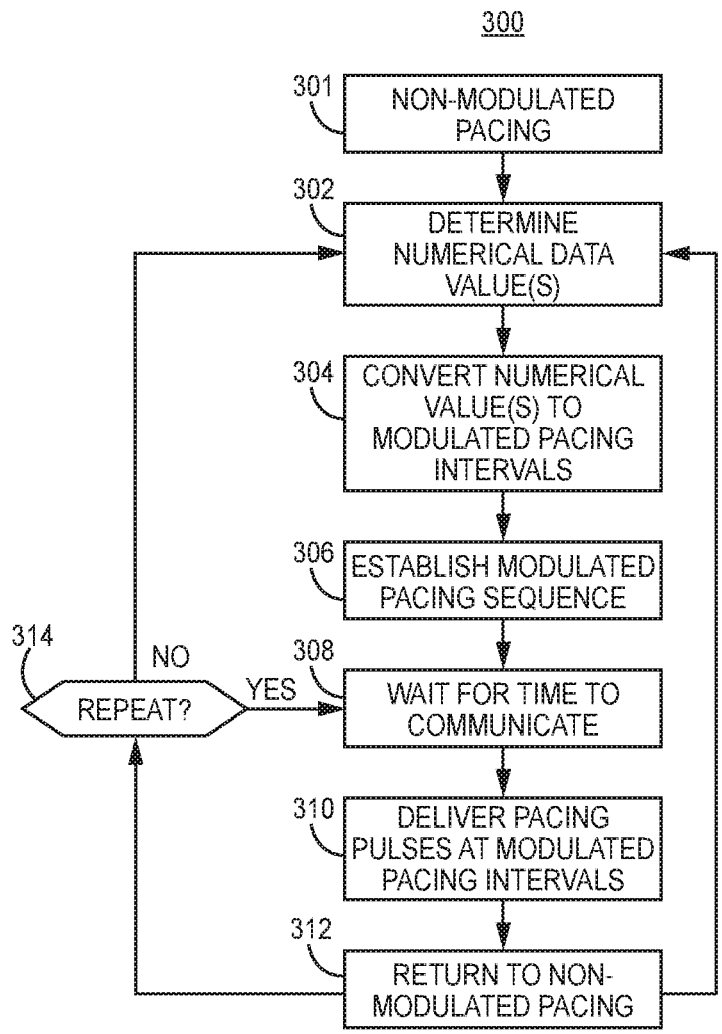
FIG. 5 is a flow chart of a method performed by the pacemaker of FIG. 1 according to one example.

FIG. 5 is a flow chart 300 of a method performed by pacemaker 14 according to one example. Initially, pacemaker 14 may be operating in a normal pacing mode at block 301, delivering pacing therapy according to programmed therapy control parameters without modulation of the pacing rate intervals. At block 302, control circuit 206 determines a numerical value of a monitored variable to be communicated via heart rate modulation. The numerical value may be determined according to a monitoring protocol, e.g., once hourly, daily, weekly or at longer, shorter or variable time intervals. The numerical values that may be determined at block 302 may be related to device diagnostics and/or patient related variables as described above. Various examples of numerical values that may be communicated by pacemaker 14 via heart rate modulation include, with no limitation intended, pacemaker battery voltage; percentage of paced events out of all paced and sensed events over a given time period; impedance measurements; and pacing capture threshold. The numerical values that may be communicated via heart rate modulation may generally include any numerical value that can be converted to a single or multi-bit word in a binary, ternary, quaternary, or other base number system or represented according to a number of pacing intervals equal to a digit of the numerical value in a base-10 number system. In some cases, a data value may be converted to multiple bytes if the data value cannot be communicated as a single multi-bit word. In other examples, the data values may be converted to multiple sets of pacing intervals each representing a numerical value of a digit between a defined range, e.g., between 0-9.

At block 304, control circuit 206 converts each numerical value to a sequence of modulated pacing intervals. In some examples, the numerical value is determined in a binary number system with one predetermined pacing interval representing a binary digit of "0" and another predetermined pacing interval representing a binary digit of "1." The second pacing rate interval representing a binary digit of "1" is different than the first pacing rate interval representing a binary digit of "0" and is distinguishable from the first pacing rate interval by the heart rate detection technique and resolution of HRM 40. The pacing rate intervals established by the IMD system, e.g., system 10 in FIG. 1, for representing binary "0" and "1" may be selected to be pacing rate intervals that are different than the pacing intervals corresponding to available programmable pacing rates or at least different than the pacing interval(s) corresponding to commonly programmed pacing rates. For instance, 60 pulses per minute is a commonly programmed lower pacing rate and corresponds to a pacing interval of 1000 ms. The pacing intervals established for use in rate modulation for data communication using a binary encoding scheme may avoid the 1000 ms interval. In one example, a pacing interval of 700 ms (corresponding to a pacing rate of about 86 pulses per minute) may be designated as a binary "1" and a pacing interval of 800 ms (corresponding to a pacing rate of 75 pulses per minute) may be designated as a binary "0." The selected pacing intervals representing a binary "0" and binary "1" may be reserved intervals that are not programmable in pacemaker 14 as an intended therapy pacing rates in some examples.

In other examples, a ternary encoding scheme may be used in which the numerical value of the monitored variable is converted from a first base number system, e.g., a binary or base 10 numerical value, to the ternary number system then converted to a sequence of pacing rate intervals representing the numerical value in the ternary number system with each one of three distinct pacing rate intervals representing a respective "0", "1" or "2" for each digit in the ternary value of the monitored variable. In some examples, therefore, control circuit 206 may be configured to convert a numerical value of the monitored variable determined in one number system (e.g., binary or base 10) to a different base number system (e.g., ternary or quaternary) then convert each digit or bit of the converted numerical value to a corresponding predetermined pacing rate interval.

The selected pacing intervals corresponding to each possible value of a digit of the numerical value may be selected and spaced apart from each other such that beat-to-beat changes between the two pacing intervals is clearly recognized by the HRM as being communication intervals as opposed to physiological changes in heart rate or normal changes in pacing rate according to a therapeutic pacing protocol. For instance normal changes in pacing rate are expected to increase gradually, decrease gradually or remain stable as opposed to a series of heart beats that includes only two specified rates (in the case of a binary value) with rate changes occurring only between those two specified rates.

In one illustrative example, the numerical value to be communicated by pacemaker 14 is the pacemaker battery voltage. The normal range of battery voltage for power source 214 may be 2.56 V to 3.2 V in one example, with 64 possible voltage values to the hundredths place. Each possible voltage value may be determined as a unique, six bit binary value as listed in TABLE I below.

TABLE I

Normal battery voltages values and corresponding six-bit binary values with converted pacing pulse interval sequences.

| BATTERY VOLTAGE | BINARY VALUE | CONVERTED PACING INTERVAL SEQUENCE (700 ms = "0" and 800 ms = "1") |
|---|---|---|
| 2.56 | 000000 | 700-700-700-700-700-700 |
| 2.57 | 000001 | 700-700-700-700-700-800 |
| 2.58 | 000010 | 700-700-700-700-800-700 |

TABLE I-continued

Normal battery voltages values and corresponding six-bit binary values with converted pacing pulse interval sequences.

| BATTERY VOLTAGE | BINARY VALUE | CONVERTED PACING INTERVAL SEQUENCE (700 ms = "0" and 800 ms = "1") |
|---|---|---|
| 2.59 | 000011 | 700-700-700-700-800-800 |
| 2.60 | 000100 | 700-700-800-700-700-700 |
| ... | ... | ... |
| 3.19 | 111110 | 800-800-800-800-800-700 |
| 3.20 | 111111 | 800-800-800-800-800-800 |

After determining the battery voltage value as a six bit binary value, the binary value is converted to a pacing rate interval sequence as shown in TABLE I where each interval represents either a digital "0" or a digital "1." As such, at block 304, after determining the numerical value of a monitored variable in a selected base number system, the numerical value is converted to a sequence of modulated pacing intervals, where each interval in the sequence corresponds to one possible value of a digit in the selected base number system. Control circuit 206 may establish a modulated pacing rate sequence at block 306 that includes the pacing rate intervals representing the numerical value and may include other information. As described below, in addition to the modulated pacing intervals representing each numerical value of one or more monitored variables to be communicated, the modulated pacing rate sequence may include modulated pacing rate intervals that represent a header, a footer, and error detection code. In other examples, the modulated pacing rate intervals may include a sequence of modulated pacing rate intervals indicating the operational status of the pacemaker 14 such as a therapy mode status, a patient status, or other categorical data that may be represented by a predetermined sequence of modulated pacing rate intervals. Control circuit 206 waits for a time to transmit the modulated pacing sequence at block 308. In some examples, the modulated pacing sequence may be delivered without delay, as long as the intrinsic heart rate or currently delivered therapy rate is less than the lowest pacing rate included in the modulated pacing sequence. The modulated pacing sequence overdrive paces the heart to control the heart rate detected by HRM 40.

In some instances, control circuit 206 may compare the intrinsic heart rate, determined based on sensed event signals received from sensing circuit 204 to the lowest heart rate associated with the modulated pacing sequence. If the intrinsic heart rate is faster than the lowest heart rate associated with the modulated pacing sequence, control circuit 206 waits at block 308 until the intrinsic heart rate falls to a rate less than the lowest modulated pacing rate included in the modulated pacing sequence. For example, RR intervals (RRIs) may be determined from the R-wave sensed event signals received from sensing circuit 204. An RRI is the time interval between two consecutively received R-waves sensed by sensing circuit 204. Control circuit 206 may wait for a threshold number of consecutive RRIs that are greater than the longest modulated pacing rate interval by a predetermined safety interval or percentage to be detected before initiating the modulated pacing rate sequence at block 310.

In other examples, control circuit 206 may wait for a predetermined time of day for initiating the modulated pacing rate sequence. The HRM 40 may be programmed or set to detect the patient's heart rate at a specified time of day. Pacemaker 14 and HRM 40 may be synchronized for data communication by programming pacemaker 14 to deliver the modulated pacing rate sequence at a specified time of day or specified time intervals that the HRM 40 is scheduled to detect heart rate. The pacemaker 14 may be programmed to start the modulated pacing rate sequence at a short time delay to ensure that the HRM 40 is operating to detect heart rate at the time the modulated pacing rate sequence is delivered.

In some cases, the scheduled time of day may be at night or when the patient is expected to be asleep. In this way, the intrinsic heart rate is expected to be less than the lowest modulated pacing rate and the patient may be less likely to perceive heart rate fluctuations or any symptoms due to the overdrive pacing required to deliver the modulated pacing rate sequence. Control circuit 80 may detect a time of day and/or detect a low patient activity level, corresponding to inactivity or rest, when pacemaker 14 includes an accelerometer or other type of patient physical activity sensor. The modulated pacing rate sequence may be delivered at any time that the patient is expected to be at rest.

In some examples, control circuit 206 may be configured to determine a sensor indicated pacing rate from the patient physical activity sensor (e.g., sensor 212 in FIG. 3) to provide rate responsive pacing that automatically adjusts the pacing rate according to patient physical activity level. Control circuit 206 may verify that the sensor indicated pacing rate is at the programmed lower rate (corresponding to rest) or at least less than lowest pacing rate included in the modulated pacing sequence at block 308. If the sensor indicated pacing rate is greater than the lowest pacing rate included in the modulated pacing rate sequence, control circuit 206 waits for the sensor indicated pacing rate to decrease before delivering the modulated pacing rate sequence at block 310.

In some cases, pacemaker 14 may be configured to detect tachyarrhythmia, e.g., tachycardia or fibrillation, and may deliver an anti-tachyarrhythmia pacing therapy (ATP). If a tachyarrhythmia is being detected and/or ATP or other therapy is being delivered to terminate a tachyarrhythmia, the control circuit 206 waits at block 308 for the heart rhythm to return to a normal sinus rhythm or a paced rhythm that is at a rate less than the lowest pacing rate included in the modulated pacing rate sequence. Accordingly, control circuit 206 may be configured to apply one or more requirements at block 308, such as time of day, patient activity level, sensor indicated pacing rate, intrinsic heart rate, cardiac rhythm, or any combination thereof, for determining the appropriate time to generate the modulated pacing sequence to transmit the monitored variable value(s) via a modulated paced heart rate.

When it is time to deliver the modulated pacing rate sequence, control circuit 206 controls pulse generator 202 to schedule and deliver cardiac pacing pulses according to the modulated sequence of pacing rate intervals at block 310. Upon completion of the modulated pacing rate sequence, delivered for communicating one or more numerical values of one or more monitored variables, pulse generator 202 returns to non-modulated pacing at block 312. The first non-modulated pacing interval after delivering a sequence of modulated pacing rate intervals may be equal to the last non-modulated pacing interval prior to the modulated pacing sequence. In other examples, the non-modulated pacing interval returned to at block 312 may be adjusted since the last non-modulated pacing interval prior to the modulated pacing sequence. For example, pacemaker 14 may have updated a sensor indicated pacing rate to provide rate responsive pacing and deliver the first pacing pulse after the modulated pacing sequence according to a non-modulated interval set to provide rate responsive pacing. In general, abrupt changes in heart rate may be avoided by delivering the first non-modulated pacing interval at a rate smoothing interval that is within a threshold difference from the ending modulated pacing interval of the sequence. It is recognized that in some instances returning to non-modulated pacing at block 312 may result in an episode of cardiac sensing with no pacing delivery required based on the programmed pacing therapy control parameters.

At block 314, control circuit 206 may determine that the modulated pacing rate sequence should be repeated. In some examples, the modulated pacing rate sequence is repeated multiple times, which may be spread out over twenty-four hours for example, to increase the likelihood of HRM 40 detecting and correctly demodulating the modulated heart rate. In other examples, the modulated pacing rate sequence may be repeated if an intrinsic sensed event occurs during the delivery of the first delivered sequence. The intrinsic heart rate may spontaneously increase, a premature contraction may occur, or non-cardiac noise may be oversensed by sensing circuit 204 (and be oversensed by HRM 40 depending on the heart rate sensor employed by HRM 40). When one or more sensed event signals are received from sensing circuit 204 by control circuit 206, control circuit 206 may determine that the modulated pacing rate sequence should be repeated.

When control circuit 206 determines that the modulated pacing rate sequence should be repeated, control circuit 206 returns to block 308 to wait for an appropriate time to repeat the modulated pacing rate sequence, which may be repeated one or more times. When no further repetitions of the modulated pacing rate sequence are required, control circuit 206 returns to block 302 to continue monitoring one or more variables and determine the next numerical value(s) to be communicated via pacing rate modulation.

It is contemplated that some device related and/or patient related variables that are monitored by pacemaker 14 may only be communicated to HRM 40 when the numerical data value is above or below a given threshold or outside a given range. For example, the battery voltage of power source 214 may be monitored by control circuit 206. An elective replacement battery voltage may be established. The elective replacement battery voltage may be a voltage level that is associated with a limited remaining functional life of the power source 214, e.g., three months, based on therapy delivery demand. The numerical value of the battery voltage may be communicated through pacing rate modulation only when the numerical value is within a predetermined range, equal to or less than the elective replacement battery voltage. In this example, the battery voltage may be determined periodically, e.g., once a day, but an indication of the numerical battery voltage value may not be included in a modulated pacing rate sequence unless it has reached a threshold relative to the elective replacement battery voltage or fallen below the elective replacement battery voltage. In other examples, a modulated pacing rate sequence may be established that indicates that the battery voltage is equal to or less than the elective replacement battery voltage and is effectively a data flag or warning that is detected by HRM 40.

As such, pacemaker 14 may be configured to monitor multiple device-related and/or patient-related variables, and control circuit 206 may be configured to determine which data values are to be communicated to HRM 40. Some data values, e.g., that fall within a normal or expected range, may not be communicated every time they are determined. A numerical data value for a particular monitored variable may be communicated via paced heart rate modulation only if outside a normal range or represents a threshold change from a preceding data value in some examples. In other examples, a numerical data value may be communicated relatively less frequently, e.g., once a week, when within a normal range and with increasing frequency, e.g., once a day, when the numerical data value is approaching or outside the normal range. Data values determined at block 302 that do not require communication to HRM 40, may be stored in pacemaker memory 210 for later communication, comparison to future measurements for detecting trends, or for radio frequency transmission during an interrogation session with external device 50, as examples.

Figure 6:
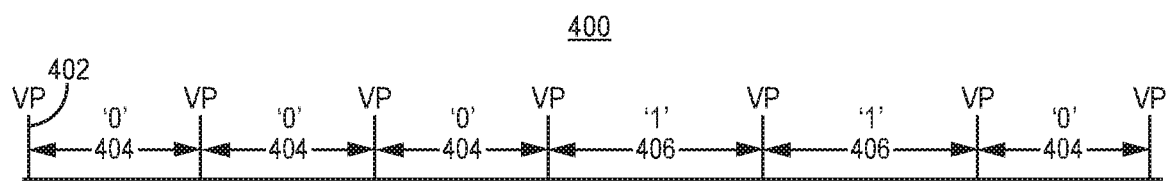
FIG. 6 is a timing diagram illustrating ventricular pacing pulses delivered at modulated pacing pulse intervals to communicate a numerical data value to a HRM.

FIG. 6 is a timing diagram 400 illustrating ventricular pacing pulses 402 delivered by pacemaker 14 at modulated pacing pulse intervals 404 and 406 to communicate a numerical data value to a HRM. In the example shown, pacing pulses 402 are delivered according to a sequence of modulated pacing pulse intervals including relatively shorter pacing pulse intervals 404 corresponding to a digital "0" and relatively longer pacing pulse intervals 406 corresponding to a digital "1" in a binary encoding scheme. The HRM in this example is configured to detect the series of heart beats occurring at the modulated rate intervals and demodulate the rate intervals to generate a binary value of 000110. The HRM may convert the binary value to a corresponding numerical base 10 value. In the example of battery voltage of Table I, the digital signal of 000110 may be converted to a battery voltage value of 2.62 V. The HRM may generate a display of the numerical value and/or transmit the numerical value to another device, such as external device 50 shown in FIG. 1. In other examples, the numerical value may be compared to an alert threshold by HRM 40. As long as the numerical value is in a normal range, HRM 40 may not take any action. If the data value is in an alert range, however, HRM 40 may generate a notification by producing a visual and/or audible alert. In examples where the HRM 40 includes therapy delivery capabilities, e.g., a pacemaker, ICD, neurostimulator, the HRM may respond to the numerical value by starting, stopping, or adjusting a therapy to account for any change in therapy being delivered by pacemaker 14. For example, if the battery voltage indicates an end of service voltage of the pacemaker power supply, the HRM detecting the modulated rate intervals may initiate a pacing or other therapy delivery function to replace a therapy no longer being delivered by pacemaker 14.

The pacing pulses 402 delivered at the modulated pacing rate intervals 404 and 406 are otherwise unchanged from pacing pulses that are delivered according to a pacing therapy. For example, pacing pulse voltage amplitude, pulse width, polarity, pulse shape and other characteristics of each ventricular pacing pulse 402 may remain constant between normal pacing therapy delivery and pacing rate modulation to communicate numerical data values. In some examples, the only pacing control parameter that is changed during data communication is the pacing pulse intervals, and therefore the pacing rate, according to a modulation protocol. Accordingly, each pacing pulse 402 shown in FIG. 6, including the first, leftmost pacing pulse that is the last pacing pulse delivered prior to modulated intervals 404 and 406, may be delivered according to identical pacing pulse amplitude, pulse width, polarity and pulse shape or waveform control parameters.

Figure 7:
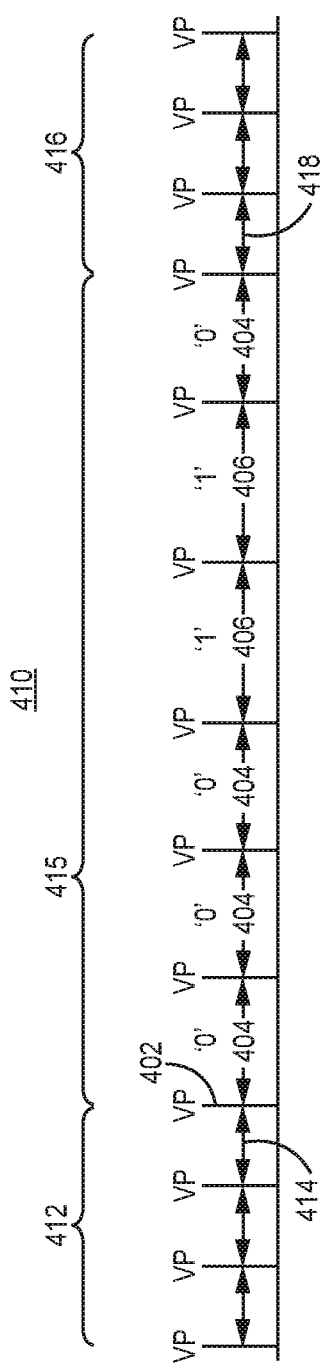
FIG. 7 is a timing diagram illustrating a modulated pacing rate sequence for communicating a numerical data value according to another example.

FIG. 7 is a timing diagram illustrating a modulated pacing rate sequence 410 for communicating data according to another example. In pacing rate sequence 410, a header 412 including one or more pacing pulses delivered at one or more predefined pacing interval(s) 414 may be delivered ahead of the modulated pacing cycles representing a numerical data value. The header 412 is a predefined sequence of one or more pacing rate intervals that is to be recognized by HRM 40 as an indication that subsequent heart rate intervals contain encoded data. The header 412 may be two or more cycles at a single predefined pacing interval, two or more cycles at two or more predefined pacing intervals in a specified pattern or a single overdrive pacing cycle at a predefined pacing interval. In the example shown, three ventricular pacing pulses are delivered at a fixed header pacing interval 414, which may be the same or different than the pacing intervals 404 and 406 designating a digital "0" and digital "1," respectively. While the header 412 is shown having a fixed pacing interval 414, two alternating intervals or other pattern may be employed as a header sequence that is recognizable by HRM 40. Starting modulated pacing rate sequence 410 with a header 412 including one or more pacing pulses delivered according to a predefined header sequence may increase the likelihood of HRM 40 successfully detecting the subsequent modulated heart rate.

Modulated pacing rate sequence 410 includes a data sequence 415 of six modulated pacing intervals representing digital zeros and ones as described in conjunction with FIG. 6. The data sequence 415 may include one or more pacing cycles representing one or more numerical values of one or more monitored variables encoded as pacing intervals according to the rate modulation protocol. The modulated pacing rate sequence 410 may be terminated by a footer 416 which may be the same or different than header 412. Footer 416 follows the data sequence 415 to indicate that the modulated pacing rate for data communication is completed. Footer 416 may include one or more pacing cycles at one or more predefined pacing intervals 418 to produce a heart rate over one or more cycles that is recognizable by HRM 40 as the footer 416 and end of heart rate modulation for data communication.

In the illustrative modulated pacing sequence 410 shown in FIG. 7, the header 412, data sequence 415, and footer 416 are shown as consecutively following one another within modulated pacing sequence 410. In other examples, one or more pacing cycles at one or more "normal" pacing pulse interval(s) may be delivered between header 412 and data sequence 415 and/or between data sequence 415 and footer 416. A "normal" pacing pulse interval is a pacing pulse interval applied according to the pacing therapy protocol as opposed to pacing pulse intervals that are modulated according to a rate modulation protocol for communication. The normal pacing pulse interval may be a programmed lower rate interval as an example. For instance, if the programmed lower rate is 60 pulses per minute, corresponding to 1000 ms, the header and footer pulse intervals 414 and 418 may be delivered at 850 ms intervals. The modulated pacing data sequence intervals 404 and 406 may be delivered at 700 and 800 ms intervals. The header 412 and footer 416 may be separated from data sequence 415 by one or more "normal" intervals at 1000 ms at the lower rate of 60 pulses per minute.

When a header precedes and/or a footer follows the data sequence of modulated pacing rate intervals, the interval and/or number of intervals included in the header or footer may include information that is demodulated by the HRM 40. For example, header 412 may be delivered according to a unique pattern or number of header pacing intervals 414 that identifies the monitored variable that is being communicated by data sequence 415. In one example, three header intervals 414 may indicate that the data sequence 415 that follows is a numerical value of the battery voltage. In another example, five header intervals 414 may indicate that data sequence 415 that follows is a numerical value of the pacing capture threshold. In other examples, two or more different pacing intervals may be included in header 412 according to a predefined sequence or pattern that is identified by HRM 40 as indicating an associated monitored variable.

Footer 416 may be common to all data sequences, independent of the specific monitored variable being communicated, and merely indicates that the data sequence is complete. In other examples, footer 416 may replicate header 412 and indicate the monitored variable being communicated as well as completion of the data sequence. In other examples, footer 416 is optional. Data sequence 415 may be followed by another header distinct from header 412 in number of header pacing intervals, duration of pacing intervals, and/or pattern of two or more different pacing intervals. This next header is delivered according to predefined pacing rate interval modulation to indicate what the next monitored variable is for which a numerical value is to be communicated by a subsequent data sequence.

In still other examples, a single header 412 may be a modulated sequence of pacing intervals that indicates the number and/or type of monitored variables to be communicated by a corresponding number of subsequent data sequences. For example, the number of pacing intervals 414 included in header 412 may indicate a corresponding number of monitored variables to be communicated in a like number of subsequent consecutive data sequences that may or may not be separated by a footer 416 or by one or more separation beats delivered according to a predefined pacing interval or as "normal" pacing intervals. For instance, the three pacing intervals 414 may indicate three monitored variable data values are to be communicated. Three subsequent data sequences may follow, which may or may not be separated by footer 416 or other separation beats. The three subsequent data sequences may be delivered according to a predefined order, e.g., battery voltage, electrode impedance, and pacing capture threshold, and according to a pacing rate modulation protocol.

In some examples, the data sequence 415 may include pacing intervals set according to a cyclic redundancy check (CRC), Hamming or other error detection code. Accordingly data sequence 415 may include additional pacing cycles modulated to the digital "0" or "1" pacing intervals, consecutive with the modulated intervals that represent the numerical data value, to provide error detection bits in the stream of pacing intervals that are detected and demodulated by HRM 40. Including error detection code with the data sequence 415, header 414, and/or footer 416 may increase the likelihood of the HRM 40 correctly detecting the modulated heart rate and reduce the likelihood of random pacing or intrinsic heart rate fluctuations from appearing as a modulated heart rate corresponding to real data.

Figure 8:
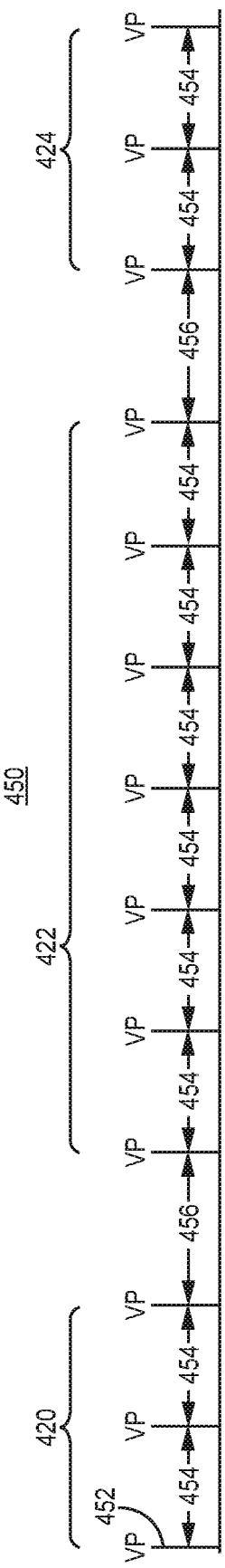
FIG. 8 is a timing diagram of a modulated pacing rate data sequence according to another example.

FIG. 8 is a timing diagram of a modulated pacing rate data sequence 450 according to another example. In this example, data sequence 450 includes one or more sets of modulated pacing intervals, with each set representing a numerical value of one digit of the numerical data value being communicated. The number of pacing cycles delivered at the modulated rate interval in each set equals the numerical value of the given digit. For example, to transmit a numerical value of 8, a set of 8 pacing cycles at a predefined modulated pacing rate interval is delivered. To transmit a multi-digit value, two or more sets of pacing intervals, one set for each digit, may be delivered sequentially in order from lowest to highest place value or from highest to lowest place value. Each set may be separated from a subsequent set, to separate the "digits" by one or more separation beats, which may be a "normal" pacing interval or a predefined separation beat pacing interval, particularly when each set is delivered at the same pacing interval as shown in FIG. 8. When different pacing intervals are used for each set indicating a digit value, separation beats may not be required.

In the illustrative example shown in FIG. 8, a numerical value of 2.62 is being communicated by data sequence 450. The numerical value 2.62 may represent 2.62 Volts, indicating the battery voltage of power source 214. A first set 420 of two modulated pacing intervals 454 are delivered to indicate the digital value of 2 in the highest place value. The pacing interval 454 is a predefined interval, e.g., 700 ms, 750 ms or 800 ms as examples, which may be a reserved pacing interval not used by a pacing therapy protocol.

The first set 420 may be separated from the second set 422 by a separation interval 456. Separation interval 456 may be a "normal" pacing cycle according to the pacing therapy, e.g., a programmed lower rate interval as described above. Separation interval 456 may alternatively be a predefined modulated interval that is different that the modulated pacing interval 454 used within a given set 420, 422 or 424 of modulated pacing intervals. A predefined number of one or more separation intervals 456 may separate the sets 420, 422 and 424 in data sequence 450.

The second set 422 of modulated pacing intervals 454 includes six intervals representing the numerical value of 6 for the second place value. The third set 424, separated from the second set 422 by one or more separation intervals 456, includes two modulated pacing intervals 454 representing a value of 2 in the third place value. Going from greatest to least place value, HRM 40 demodulates a numerical value of 2.62 from the data sequence 450.

The data sequence 450 may be preceded by a header and/or terminated by a footer as generally described above in conjunction with FIG. 7 to indicate the onset and or termination of the data sequence 450. In this example, the header and/or footer may include modulated information indicating, e.g., the number of data sets, i.e., the number of place values, represented by the data sequence 450 and/or the order from highest to lowest or lowest to highest place values.

Depending on the possible range of a numerical value of a given monitored variable, the value of a digit in a given place value may be inferred by HRM 40 without being represented by a set of pacing intervals within data sequence 450. For example, since a normal range of battery voltage is from 2.56 to 3.20, a set of modulated intervals representing the numerical tenths place value and a set representing the numerical hundredths place value may be included in data sequence 450. A set of modulated intervals representing the numerical ones place value may be omitted. Since any tenths place value of 0.5 or higher must be preceded by a value of 2 in the ones place, and any tenths place value of 0.2 or less must be preceded by a value of 3 in the ones place to span the normal range of battery voltages from 2.56 to 3.20, the HRM 40 may infer the ones place value based on the tenths place value. Thus, in some cases, all battery voltages may be communicated by a data sequence including two sets of modulated pacing intervals, with each set including the number of the modulated pacing intervals equal to the numerical digit of the respective tenths or hundredths place value. Furthermore, when the sets are transmitted from highest to lowest place value for instance, a single set of pacing intervals at the modulated pacing rate interval 454 may be interpreted by the HRM 40 as representing the tenths digit with the hundredths digit being a numerical value of zero, in this example of battery voltage. In other multi-digit data values, a specified number of separation intervals 456 may indicate a numerical value of zero for a place value that is in between two other non-zero place values. When the numerical value is zero for two consecutive place values, for example a battery voltage of 3.00, and the ones place value is omitted to be inferred by HRM 40, the numerical values of two consecutive zeros in the tenths and hundredths places may be represented by predefined series of separation intervals 456 delivered at a modulated pacing interval different than the modulated pacing interval 454 used within a set of pacing intervals such as sets 420, 422 and 424.

While two examples of pacing rate modulation for producing a data sequence that is detected by HRM 40 as modulated heart rates that can be demodulated into numerical data values have been described in conjunction with FIGS. 6, 7 and 8, it is recognized that numerous protocols are conceivable for modulating the pacing rate to represent a numerical value of a monitored variable. The particular modulation protocol may be defined based on the heart rate detection method employed by HRM 40. For instance, in the examples of FIGS. 6, 7 and 8, it is assumed that HRM 40 is capable of detecting the heart rate beat by beat to distinguish the heart rate interval from one cardiac cycle to the next and therefore detect each modulated cardiac cycle length and distinguish it from a different modulated cardiac cycle length and cycle lengths (or heart rates) corresponding to "normal" pacing intervals of the programmed pacing therapy and even intrinsic heart beats.

In other examples, HRM 40 may detect heart rate by counting a number of PPG pulses, bioimpedance pulses, R-waves or other heart rate sensor signal feature indicative of a heartbeat over a given time interval to convert the number of heartbeats counted over the given time interval to a heart rate. Conversely, HRM 40 may be configured determine the time interval over which a predetermined number of sensor signal pulses or R-waves occurs and convert that time interval to a heart rate. In still other examples, HRM 40 may use FFT or other techniques for deriving a frequency of the heart rate sensor signal and converting the frequency to a heart rate. In these examples where the heart rate is detected over a fixed or variable time interval by counting heart beats or performing Fourier transform or other techniques for deriving a heart rate from the sensor signal, the pacing rate modulation communication protocol may involve delivering a fixed, modulated pacing rate over a time interval that is sufficiently long to be detected as the modulated heart rate by the HRM 40 as opposed to a single beat by beat heart rate detection as described above in conjunction with FIGS. 6-8.

Figure 9:
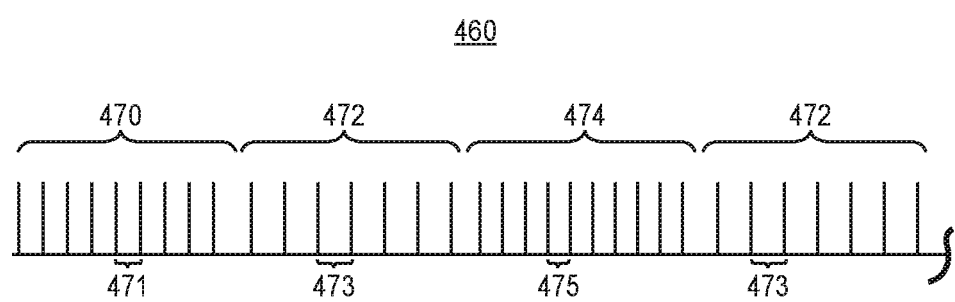
FIG. 9 is a timing diagram of pacing rate modulation according to another example.

FIG. 9 is a timing diagram 460 of pacing rate modulation according to another example. Rather than delivering a modulated pacing rate interval for a single pacing cycle to be detected as a modulated heart rate by the HRM 40, a modulated pacing rate interval may be delivered for a plurality of cycles in order to enable the HRM to detect the corresponding heart rate. In this case, pacing pulses are delivered at a modulated pacing rate interval for a predetermined number of pacing cycles or a predetermined time interval to enable HRM 40 to detect the heart rate corresponding to the modulated pacing rate by counting pulses over a fixed or variable time interval as described above or performing FFT or other frequency analysis. For example, during a first data time segment 470, a fixed pacing rate at a first modulated pacing rate interval 471 may be delivered and detected by the HRM 40 as digital "0" (or "1"). The fixed heart rate detected over data time segment 470 may be demodulated to a numerical value of a monitored variable or one of its digits. A second modulated pacing rate may be delivered over a second data time segment 474 to be detected as a different heart rate by HRM 40. The pacing rate interval 475 of data time segment 474 may represent a digital "1" (or "0") in a binary encoding scheme or be assigned to a numerical value in another number system, such as a 0, 1, 2 or 3 in a base 4 system.

The two modulated data time segments 470 and 474 are shown separated by separation time segment 472 that may include pacing according to the programmed pacing therapy, e.g., according to the programmed lower rate interval. In other examples, separation time segment 472 may include pacing at a uniquely defined overdrive pacing rate interval 473 different than the modulated pacing rate intervals 471 and 475 of data time segments 470 and 474. The second data time segment 474 is followed by another separation time segment 472 and the pacing modulation sequence 460 may continue with additional modulated pacing rate time intervals delivered over predetermined time segments as needed to complete communication of one or more numerical data values of a corresponding number of monitored variables. In some instances, the separation time segment 472 may include intrinsic heart beats, e.g., that occur at a heart rate that is faster than the programmed lower rate but may be slower than the modulated pacing rate intervals 471 and 475.

The overall total time and number of modulated pacing cycles required to communicate a numerical value of a single monitored variable using the technique of FIG. 9 may be longer than the examples of FIGS. 6, 7 and 8, however the longer time segments at a fixed modulated interval may be required depending on the heart rate detection method employed by HRM 40. Time segments 470, 472 and 474 may be set to be long enough to cover an entire sampling interval used by HRM 40 for detecting one heart rate. For example, if HRM 40 samples the heart rate sensor signal every 2 seconds to determine a heart rate value, each data time segment 470 and 474 may be 4 seconds long or more to promote reliable detection of the corresponding heart rate by HRM 40, sampling once every 2 seconds. Control circuit 206 may extend a data time segment 470 or 474 in response to an increase in intrinsic heart rate during the time segment. For example, if one or more R-wave sensed event signals are received by control circuit 206 from sensing circuit 204 during time segment 470, time segment 470 may be increased to three times the sampling interval, e.g., 6 seconds, to enable HRM 40 to discard a rate from one sampling interval that changed unexpectedly. Any of the pacing rate modulation examples presented in conjunction with FIGS. 6-9, or combinations or variations thereof, may be performed in the process of FIG. 5 according to a modulated pacing rate communication protocol.

Figure 10:
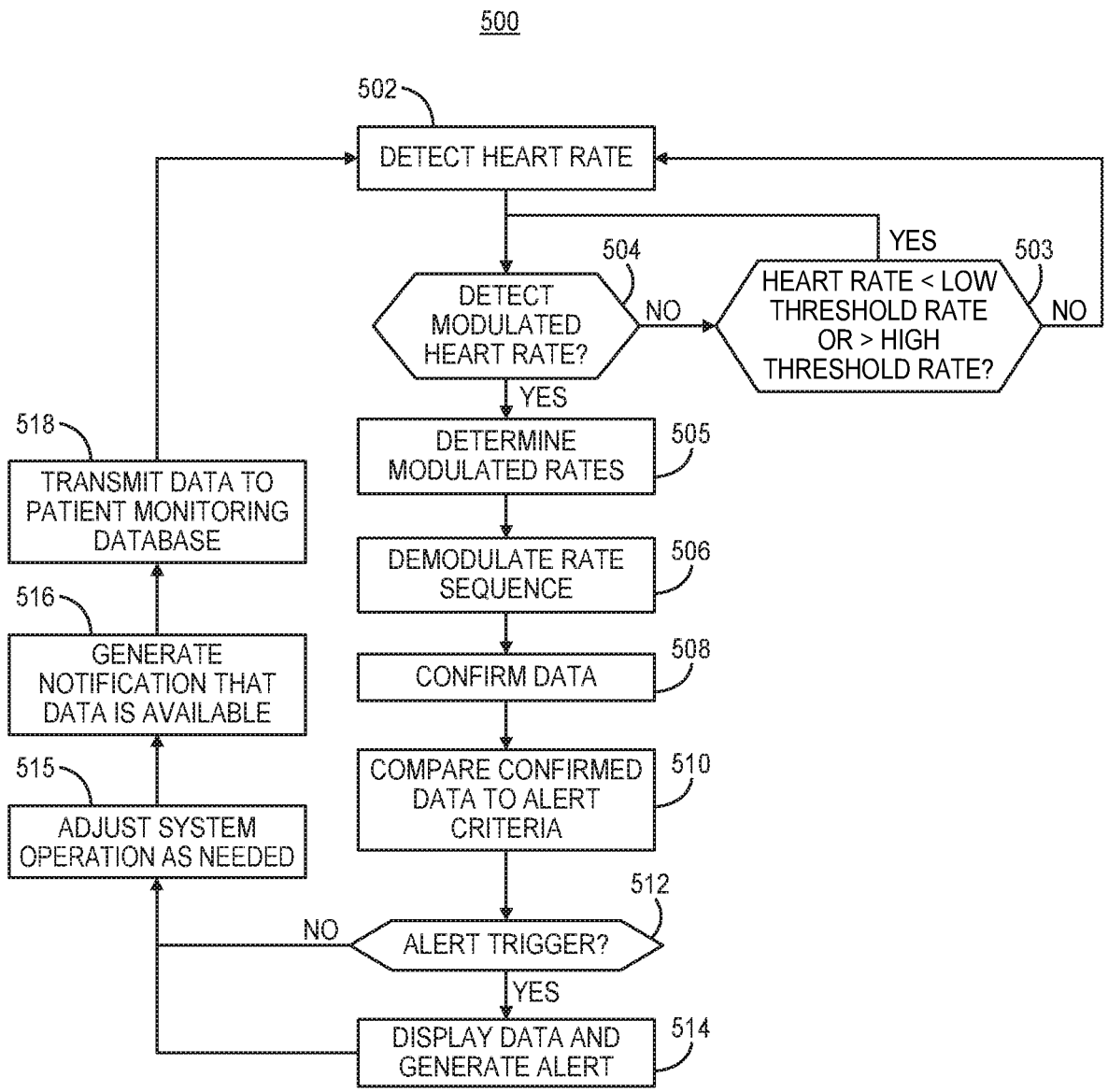
FIG. 10 is a flow chart of a method that may be performed by a heart rate monitor for detecting heart rate and demodulating the detected heart rate to determine a data value according to one example.

FIG. 10 is a flow chart 500 of a method that may be performed by HRM 40 for detecting heart rate and demodulating the detected heart rate to determine a numerical data value according to one example. At block 502, HRM 40 determines the heart rate according to a heart rate monitoring protocol using the heart rate detection technique implemented in HRM 40. For example, HRM 40 may be configured to detect the heart at scheduled times of day, at predetermined time intervals, or on an ongoing basis. In order to detect a modulated heart rate due to a modulated pacing rate sequence delivered by pacemaker 14, HRM 40 may determine the time interval between consecutive pulses or beats, i.e. the cardiac cycle length, detected by the heart rate sensor implemented in HRM 40. For example, RRIs may be determined by HRM 40 when HRM 40 includes electrodes for sensing an ECG signal or cardiac cycle lengths may be determined between pulse peaks when HRM 40 includes an optical sensor for PPT. In other examples, HRM 40 may detect the heart rate over a sampling interval using FFT or other techniques.

At block 454, HRM 40 determines if a heart rate is detected that corresponds to a modulated heart rate used for data communication. Processor 104 of HRM 40 may compare individual heart rate intervals or a detected heart rate to the modulated pacing rates established for data communication. Modulated pacing rates corresponding to the pacing rate intervals used by pacemaker 14 may be stored in memory 106 of HRM 40 for comparison to detected heart rates for recognizing a modulated heart rate. For example, a heart rate corresponding to the modulated pacing rate interval established as a digital "0" or a digital "1" or a known header interval may be detected over one or more cardiac cycles or a heart rate sampling interval. If a heart rate that corresponds to a modulated pacing rate interval is not detected at block 504, the HRM 40 does not look for additional modulated heart rates and returns to block 502 to monitor the heart rate according to the heart rate monitoring protocol.

In some examples, when a heart rate corresponding to a modulated pacing rate is not detected, HRM 40 may compare the detected heart rate to a threshold rate at block 503. If the detected heart rate is less than a low threshold rate or greater than a high threshold rate at block 503, HRM 40 may remain enabled for heart rate detection by returning to block 504 to continue to detect the heart rate beat-by-beat or sampling interval by sampling interval to wait for a modulated heart rate. In some cases, a very low heart rate or very high heart rate, e.g., a heart rate less than 40 beats per minute or greater than 140 beat per minute, or other established thresholds appropriate for the patient, may indicate a concerning condition. Pacemaker 14 may be configured to communicate one or more patient related and/or device related monitored variables which may be useful in detecting or diagnosing a serious patient condition associated with the low or high heart rate that may warrant medical attention. In anticipation of important patient-related or device-related monitored variables being communicated, HRM 40 may remain enabled to detect a modulated heart rate when an abnormal heart rate is detected.

If a heart rate corresponding to a modulated pacing rate interval is detected at block 504, processor 104 determines the heart rate for subsequent consecutive cardiac cycles, beat-by-beat, or subsequent heart rate sampling intervals depending on the heart rate detection technique that is implemented. Consecutive heart rates may be determined until a threshold number of detected heart rates do not correspond to a modulated pacing rate interval. For example the heart rate may be detected one or more times (on one or more cardiac cycles or sampling intervals) corresponding to the pacing lower rate or otherwise not matching the modulated pacing rate intervals defined by the modulation scheme. When a threshold number of non-modulated heart rate detections are made, the HRM 40 may or may not continue determining the heart rate on a continuous basis, e.g., on consecutive cardiac cycles or consecutive sampling intervals, in accordance with the normal heart rate monitoring protocol performed by HRM. In some examples, HRM 40 detects a modulated heart rate at block 504 by detecting a header including one or more modulated rate intervals as described in conjunction with FIG. 7. Consecutive heart rates, beat-by-beat or over consecutive sampling intervals, may be determined until a threshold number of non-modulated heart rates are detected, until a predefined number of expected modulated heart rates are detected based on information included in the header, or until a footer is detected.

As the modulated heart rates are detected at block 504, or after a complete modulated heart rate sequence is detected, the processor 104 demodulates the sequence of heart rates by converting each rate to a corresponding value according to the encoding scheme. For example, each single cardiac cycle length (e.g., corresponding to the data sequence in FIG. 6) may be converted to a binary "0" or "1" to determine a binary word that is converted to a numerical (base 10) value of the monitored variable. In other examples, HRM detects a set of cardiac cycle lengths (e.g., corresponding to the data sequence in FIG. 8) and converts the number of cardiac cycles to the value of one digit of the numerical value of the monitored variable. In still other examples, HRM 40 converts a heart rate detected over one or more sampling intervals to a corresponding binary value (or other base number system). Consecutive cardiac cycles, sets of cardiac cycles, or sampling intervals are converted to corresponding digit values.

At block 508, HRM processor 104 may be configured to confirm the received data which may include error detection coding as described previously. Header and/or footer detection may be used to verify that a demodulated data sequence is valid. For example, if the header indicates a specific monitored variable data value is being communicated, but the subsequently detected and demodulated heart rates do not correspond to a valid numerical value of the monitored variable (e.g., outside a specified range of possible values), the HRM processor 104 may determine the that the numerical value is invalid. In other examples, HRM 40 may be configured to detect an outlier of a monitored variable. For example, if a demodulated numerical value of the monitored variable is within a range of possible values but is greater than a threshold change from a preceding value, HRM 40 may flag the data value as a possible outlier. If the next numerical value of the monitored variable received after the flagged value is within a threshold change of the first preceding value, the intervening flagged data value may be deemed an outlier and considered a spurious or invalid data value.

The HRM 40 may provide a variety of responses to the demodulated data values. In some examples, a numerical data value is compared to alert criteria at block 510. The numerical data value may be compared to an alert range indicating that medical follow-up is recommended. If the alert criteria are satisfied, as determined at block 512, the HRM 40 may generate a display of the data and/or generate an audible, visual or other sensory alert such as a vibration at block 514 to notify the patient to follow up with a clinician.

In some examples, the HRM 40 may be configured to adjust a therapy that is delivered by the IMD system, e.g., system 10 shown in FIG. 1. HRM 40 may be configured to adjust a therapy either directly or via communication with another medical device included in the IMD system. For instance, when the HRM is implemented as an ICD, the ICD may enable a pacing function to replace a pacing function provided by pacemaker 14 when the numerical value of a monitored battery voltage meets alert criteria or other therapy adjustment criteria. When the battery voltage reaches a threshold level, e.g., an elective replacement voltage or end of service voltage, the HRM may determine that pacing therapy delivered by pacemaker 14 may be stopped or adjusted to a power conserving pacing mode. The HRM may adjust its own pacing mode or other therapy based on the demodulated numerical value of the monitored variable. In other examples, the HRM may transmit a therapy adjustment command to another medical device, e.g., via external device 50, to cause a therapy delivery adjustment at block 515.

In another example, when the numerical value of a monitored parameter is demodulated to a value that indicates that pacemaker 14 may be performing temporary operations, the HRM may respond to the demodulated value by adjusting the therapy delivery at block 515. For example, a transmitted value of a pacing capture threshold may be an indication that a pacing capture threshold test is going to be performed by pacemaker 14. The HRM may adjust a pacing therapy, cardiac rhythm detection or other functionality of the IMD system to avoid interference with the capture test or confounding rhythm detection results. As such, the HRM may adjust its own operation or generate a command or notification that an adjustment by another medical device included in the IMD system is needed in response to the demodulated numerical value of the monitored variable.

In still other examples, the need for a system operation adjustment may be based on any categorical data communicated according to predefined sequences of modulated pacing rate intervals. For example, the current pacing mode of pacemaker 14 may be demodulated by HRM from the modulated heart rates and based on the current pacing mode, the pacing mode of the HRM or another medical device may be adjusted at block 515. For example, when the HRM is an extracardiovascular ICD, the ICD may enable anti-tachycardia therapy, back-up pacing therapy, or other pacing therapy previously delivered by pacemaker 14 when the pacing mode of pacemaker 14 has changed, e.g., due to a low battery voltage condition.

Each time data is received, whether or not alert criteria are met and/or system operation adjustment is needed, the HRM 40 may generate a notification that new data is available at block 516. The user may view the data using an application programmed in the HRM 40. The application may allow the user to open a window of a display, e.g., a graph or table, of the new data values, which may include historical data and/or indicators of normal ranges of the displayed numerical data values.

At block 518, the HRM 40 may transmit the data values to a patient monitor or external device, such as external device 50, or to a centralized patient monitoring database, e.g., via a BLUETOOTH® connection. The transmitted data values may exclude data values identified as out of range or spurious values identified at block 508. In some examples, HRM 40 may transmit detected modulated heart rates or heart rate intervals without demodulating the heart rates or heart rate intervals prior to transmission. Demodulation may be performed by a receiving device, e.g., external device 50 or another pacemaker, implantable cardioverter defibrillator or other medical device, or a centralized database. In this way, BLUETOOTH® capabilities of HRM 40 may be utilized for transmitting data communicated from pacemaker 14 without requiring pacemaker 14 to have or utilize BLUETOOTH® or other RF transmission capabilities, saving space and/or power consumption of pacemaker 14.

Figure 11:
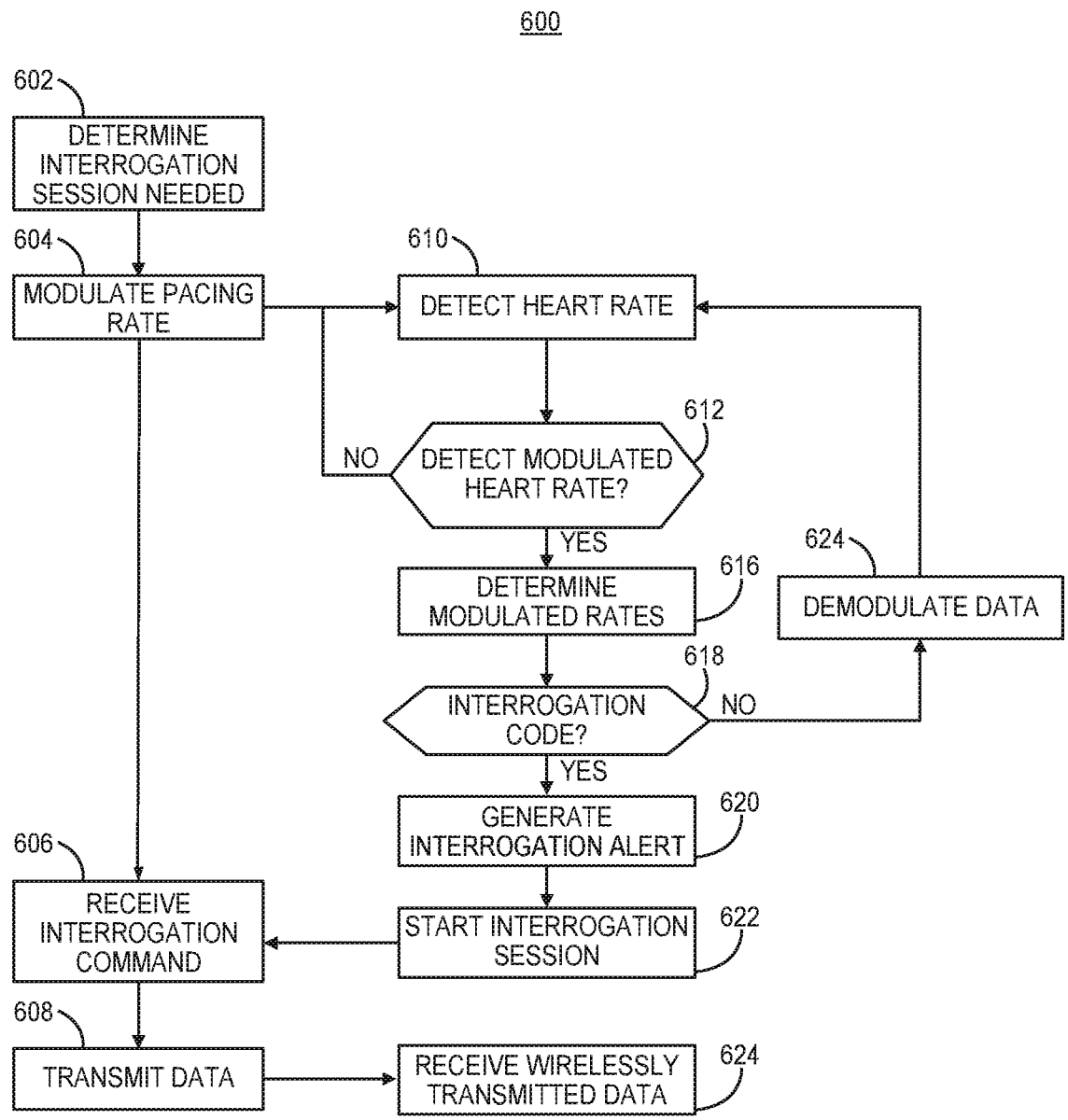
FIG. 11 is a flow chart of a method performed by the system of FIG. 1 according to another example.

FIG. 11 is a flow chart 600 of a method performed by system 10 of FIG. 1 according to another example. In some examples, pacemaker 14 may determine that an interrogation session is needed (block 602) and modulate the pacing rate according to an interrogation command code at block 604. For instance, pacemaker 14 may determine that an interrogation session is needed according to a regular schedule stored in memory 210, e.g., once per day, once per week etc. The interrogation session is scheduled to retrieve data from pacemaker 14 using wireless RF transmission by an external device, e.g., either HRM 40 or external device 50. Control circuit 206 may determine that an interrogation session is needed at a scheduled time at block 602 and modulate the pacing rate according to an interrogation command code at block 604. In other examples, control circuit 206 may determine that an interrogation session is needed at block 602 because a scheduled interrogation session is past due or an expected interrogation session has not yet occurred. Control circuit 206 may not modulate the pacing rate at block 604 to communicate an interrogation command code to HRM 40 unless an expected interrogation session has not occurred or is past due by at least a threshold time interval, e.g., 8 hours, 24 hours or other threshold time interval.

In other examples, pacemaker 14 may determine that an interrogation session is needed at block 602 in response to detecting a patient-related or device-related event. For instance, pacemaker 14 may detect an arrhythmia episode, a change in pacing impedance or capture threshold, an out of range monitored parameter or other event that may warrant medical attention. In response to an event that warrants data transmission via wireless RF transmission as opposed to only pacing rate modulation, as described in the various examples given above, control circuit 206 may modulate the pacing rate at block 604 according to an interrogation command code to initiate the interrogation process. The modulated pacing rate for communicating an interrogation command code at block 604 may be repeated multiple times until an RF interrogation command transmitted by another device is received by telemetry circuit 208.

At block 610, HRM 40 detects the patient's heart rate. HRM 40 determines if the detected heart rate corresponds to a modulated heart rate. A modulated heart rate is detected at block 612 based on detection of a heart rate or heart rate intervals corresponding to designated, reserved rates or intervals used for communication or detection of a header or specified pattern of heart rates or rate intervals. When a modulated heart rate is detected at block 612, HRM 40 determines the modulated rates and compares the modulated rate or pattern to an interrogation command code at block 618. A pre-defined reserved heart rate, e.g., 70 beats per minute, for a predefined number of heart beats or time intervals may correspond to the interrogation command code. The interrogation command code may be defined according to a specified number of heart beats or specified number of heart rate time intervals including one or more specified heart rates occurring in a specified pattern.

When the interrogation command code is not detected at block 618, HRM 40 may demodulate the detected modulated heart rate to determine numerical values of monitored parameters as described above in conjunction with any of FIGS. 5-10. When the interrogation command code is detected at block 618, HRM 40 generates an interrogation alert at block 620. The interrogation alert may by a visual display or audible sound produced by HRM 40 to alert the patient than an interrogation session is needed. The patient may be instructed to respond to an alert by taking any steps necessary to enable an interrogation session to occur. For example, the patient may be required to open an application on HRM 40 or external device 50 and/or hold HRM 40 or external device 50 within a specified proximity to pacemaker 14, e.g., within one foot.

In other examples, the interrogation alert produced by HRM 40 may be a signal transmitted from HRM 40 to another external device, e.g., external device 50 shown in FIG. 1. The external device 50 may respond to receipt of the interrogation alert by automatically starting an interrogation session at block 620 by transmitting a wake-up command or other signal to pacemaker 14 to establish a bidirectional communication link with pacemaker 14. Additionally or alternatively, external device 50 may respond to receipt of the interrogation alert transmitted from HRM 40 by generating a patient alert, e.g., a notification on a display of external device 50, text message, audible alarm or other patient notification method. In this case, the patient may be instructed to respond to the alert from external device 50 by taking necessary steps to enable the interrogation session to occur.

At block 622, external device 50 starts the interrogation session by establishing a bidirectional communication link and transmitting an interrogation command to pacemaker 14. In response to receiving the interrogation command at block 606, pacemaker 14 transmits data via wireless RF transmission by telemetry circuit 208. Data that may be transmitted during an interrogation session may include data that is not available for communication via pacing rate modulation alone. Such data may generally include larger amounts of data such as recorded cardiac electrical signal episodes and marker channel data, detected rhythms, therapy delivery and sensing control parameters, sensing and pacing data, or other data stored by pacemaker 14 in memory 210 or cardiac electrical signals transmitted in real time.

The operation of system 10 is improved when pacemaker 14 is configured to determine that an interrogation session is needed and communicate an interrogation command code via pacing rate modulation for detection by HRM 40 because power is conserved by avoiding frequent wakeups of a telemetry circuit of pacemaker 14 for listening for a ping or communication request from another device. The power required for pacemaker 14 to initiate a communication session by modulating the pacing rate for communicating an interrogation command is minimal since it is the same or similar power used to deliver the pacing therapy. The overall system 10 is further improved because compliance of the patient is promoted in retrieving data from pacemaker 14 for review by a clinician. Increased patient compliance enables the clinician to confirm appropriate pacemaker operation and identify any changes needed to sensing and/or therapy operations of pacemaker 14 in order to best meet the patient's needs. The reduced size of an intracardiac pacemaker, such as pacemaker 14 shown in FIG. 1, may limit the power available for wireless data transmission, such as via BLUETOOTH®, and the depth of implant of an intracardiac pacemaker may limit the range of RF signals being transmitted. The ability of pacemaker 14 to transmit larger amounts of data to an external device is improved by communicating the interrogation command via pacing rate modulation first to subsequently promote successful and efficient RF data transmission to an external device that is placed within the transmission range of pacemaker 14.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, an 1 MB system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device system, comprising:
an implantable medical device comprising:
 a control circuit configured to:
  determine a numerical value of a monitored variable that is monitored by the implantable medical device based on a monitoring protocol; and
  convert the numerical value of the monitored variable to a data sequence comprising a plurality of modulated stimulation rate intervals; and
 a pulse generator configured to deliver a plurality of electrical stimulation pulses according to a header including at least one modulated stimulation rate interval and the plurality of modulated stimulation rate intervals of the data sequence to cause a modulated rate of activation of an excitable tissue of a patient that corresponds to the at least one modulated stimulation rate interval of the header and the plurality of modulated stimulation rate intervals of the data sequence, the modulated rate of activation being detectable by a rate monitor for demodulation of the modulated rate of activation to the numerical value of the monitored variable.

2. The system of claim 1, wherein:
the implantable medical device is configured to deliver cardiac pacing pulses;
the control circuit is configured to convert the numerical value to the data sequence by converting the numerical value to a plurality of modulated cardiac pacing rate intervals; and
the pulse generator is configured to deliver the plurality of electrical stimulation pulses as cardiac pacing pulses according to the plurality of modulated cardiac pacing rate intervals to cause a modulated heart rate of the patient, the modulated heart rate being detectable by a heart rate monitor.

3. The system of claim 2, wherein the control circuit is configured to convert the numerical value to the data sequence by:
converting the numerical value from a first base number system to a second base number system comprising a plurality of digits in the second base number system; and
converting each digit in the second base number system to a corresponding modulated pacing rate interval.

4. The system of claim 2, wherein the control circuit is configured to convert the numerical value to the data sequence of modulated pacing rate intervals by:
determining a binary value of the numerical value, the binary value having a predetermined number of digits; and
converting the binary value to the sequence of modulated pacing rate intervals by setting at least one pacing interval to represent one digit of the predetermined number of digits, the at least one pacing interval being set to one of a first pacing rate interval to represent a binary digit of zero in the binary value and a second pacing rate interval representing a binary digit of one, the first pacing rate interval different than the second pacing rate interval.

5. The system of claim 2, wherein the control circuit is configured to convert the numerical value to the data sequence comprising the plurality of modulated pacing rate intervals by:
setting a number of the plurality of the modulated pacing rate intervals to a fixed pacing interval wherein the number equals a value of a digit of the numerical value of the monitored variable.

6. The system of claim 2, wherein the numerical value is a multi-digit value and the control circuit is configured to convert the numerical value to the data sequence comprising the plurality of modulated pacing rate intervals by:
converting a first value of a first digit of the multi-digit numerical value to at least one respective modulated pacing rate interval; and
dropping a second value of a second digit of the multi-digit numerical value from the data sequence, the dropped second value of the second digit being inferable from the first value of the first digit of the multi-digit numerical value.

7. The system of claim 2, wherein the pulse generator is configured to deliver the plurality of pacing pulses according to the data sequence by:
delivering pacing pulses at a fixed pacing rate interval for a time interval to produce a heart rate for the time interval, the heart rate representing a value of a digit of the numerical value.

8. The system of claim 2, wherein the control circuit is configured to convert the numerical value to a data sequence by:
scheduling consecutive sets of modulated pacing rate intervals, wherein each set of modulated pacing rate intervals comprises at least one modulated pacing rate interval representing a single digit of the numerical value; and
including at least one separation pacing interval between the consecutive sets, the separation interval being different than the modulated pacing rate intervals of the consecutive sets of modulated pacing rate intervals.

9. The system of claim 2, wherein:
the pacemaker further comprises a cardiac electrical signal sensing circuit configured to sense cardiac event signals; and
the pulse generator is configured to repeat delivering at least a portion of the plurality of pacing pulses according to the data sequence in response to the cardiac electrical signal sensing circuit sensing a cardiac event signal during the data sequence.

10. The system of claim 2, further comprising a heart rate monitor, the heart rate monitor configured to:
detect the modulated heart rate;
determine the numerical value of the monitored variable by demodulating the detected modulated heart rate; and
generate a response to the determined numerical value by at least one of: wirelessly transmitting the numerical value to a patient monitoring device, generating a display of the numerical value, generating an alert, and adjusting a therapy delivery mode of the system.

11. The system of claim 1, wherein the pulse generator is further configured to deliver the plurality of electrical stimulation pulses comprising at least one stimulation rate interval that is not modulated between the header and the data sequence.

12. The system of claim 1, wherein the control circuit is configured to set the at least one modulated stimulation rate interval of the header to indicate information about the data sequence.

13. The system of claim 1, wherein the control circuit is further configured to set at least one error detection stimulation rate interval in the data sequence of the plurality of modulated stimulation rate intervals.

14. The system of claim 1, wherein:
the control circuit is further configured to modulate a plurality of electrical stimulation rate intervals according to an interrogation command code sequence;
the pulse generator is further configured to deliver the modulated plurality of electrical stimulation rate intervals according to the interrogation command code sequence for detection by the rate monitor; and
the implantable medical device further comprises a telemetry circuit configured for bi-directional wireless communication with an external device, the telemetry circuit configured to receive an interrogation command from the external device subsequent to delivery of the modulated plurality of electrical stimulation rate intervals according to the interrogation command code sequence.

15. A method comprising:
determining by an implantable medical device a numerical value of a monitored variable that is monitored by the implantable medical device based on a monitoring protocol;
converting by a control circuit of the implantable medical device the numerical value of the monitored variable to a data sequence comprising a plurality of modulated stimulation rate intervals; and
delivering, by a pulse generator of the implantable medical device, a plurality of electrical stimulation pulses according to a header including at least one modulated stimulation rate interval and the plurality of modulated stimulation rate intervals of the data sequence to cause a modulated rate of activation of an excitable tissue of a patient that corresponds to the at least one modulated stimulation rate interval of the header and the plurality of modulated stimulation rate intervals of the data sequence, the modulated rate of activation detectable by a rate monitor for demodulation of the modulated rate of activation to the numerical value of the monitored variable.

16. The method of claim 15, wherein:
converting the numerical value to the data sequence comprises converting the numerical value to a plurality of modulated cardiac pacing rate intervals; and
delivering the plurality of electrical stimulation pulses comprises delivering a plurality of cardiac pacing pulses according to the plurality of modulated cardiac pacing rate intervals to cause a modulated heart rate of the patient, the modulated heart rate being detectable by a heart rate monitor.

17. The method of claim 16, wherein converting the numerical value to the data sequence comprises:
converting the numerical value from a first base number system to a second base number system comprising a plurality of digits in the second base number system; and
converting each digit in the second base number system to a corresponding modulated pacing interval.

18. The method of claim 16, wherein converting the numerical value to the data sequence of modulated pacing rate intervals comprises:
determining a binary value of the numerical value, the binary value having a predetermined number of digits; and
converting the binary value to the sequence of modulated pacing rate intervals by setting at least one pacing interval to represent one digit of the predetermined number of digits, the at least one pacing interval being set to one of a first pacing rate interval to represent a binary digit of zero in the binary value and a second pacing rate interval representing a binary digit of one, the first pacing rate interval different than the second pacing rate interval.

19. The method of claim 16, wherein converting the numerical value to the data sequence comprising the plurality of modulated pacing rate intervals comprises:
setting a number of the plurality of the modulated pacing rate intervals to a fixed pacing rate interval wherein the number equals a value of a digit of the numerical value of the monitored variable.

20. The method of claim 16, wherein the numerical value is a multi-digit value and converting the numerical value to the data sequence comprising the plurality of modulated pacing rate intervals comprises:
converting a first value of a first digit of the multi-digit numerical value to at least one respective modulated pacing rate interval; and
dropping a second value of a second digit of the multi-digit numerical value from the data sequence, the dropped second value of the second digit being inferable from the first value of the first digit of the multi-digit numerical value.

21. The method of claim 16, wherein delivering the plurality of pacing pulses according to the data sequence comprises:
delivering pacing pulses at a fixed pacing rate interval for a time interval to produce a heart rate for the time interval, the heart rate representing a value of a digit of the numerical value.

22. The method of claim 16, wherein converting the numerical value to a data sequence comprises:

scheduling consecutive sets of modulated pacing rate intervals, wherein each set of modulated pacing rate intervals comprises at least one modulated pacing rate interval representing a single digit of the numerical value; and including at least one separation pacing interval between the consecutive sets, the separation interval being different than the modulated pacing rate intervals of the consecutive sets of modulated pacing rate intervals.

23. The method of claim 16, further comprising:

sensing a cardiac event signal by a cardiac electrical signal sensing circuit of the pacemaker; and repeating delivering at least a portion of the plurality of pacing pulses according to the data sequence in response to the cardiac electrical signal sensing circuit sensing a cardiac event signal during the data sequence.

24. The method of claim 16, further comprising:

detecting the modulated heart rate by a heart rate monitor;

determining the numerical value of the monitored variable by demodulating the detected modulated heart rate; and generating a response to the determined numerical value by at least one of: wirelessly transmitting the numerical value to a patient monitoring device, generating a display of the numerical value, generating an alert, and adjusting a therapy delivery mode of a medical device.

25. The method of claim 15, further comprising setting the at least one modulated stimulation rate interval of the header to indicate information about the data sequence.

26. The method of claim 15, further comprising delivering at least one error detection stimulation rate interval in the data sequence of the plurality of modulated stimulation rate intervals.

27. The method of claim 15, further comprising:

modulating a plurality of electrical stimulation rate intervals according to an interrogation command code sequence;

delivering, by the pulse generator, the modulated plurality of electrical stimulation rate intervals according to the interrogation command code sequence for detection by the rate monitor; and receiving an interrogation command from an external device by a telemetry circuit of the implantable medical device subsequent to delivery of the modulated plurality of electrical stimulation rate intervals according to the interrogation command code sequence, the telemetry circuit configured for bi-directional wireless communication with the external device.

28. A non-transitory, computer-readable storage medium comprising a set of instructions which, when executed by a control circuit of an implantable medical device, cause the device to:

determine a numerical value of a variable that is monitored by the implantable medical device according to a monitoring protocol;

convert the numerical value to a data sequence comprising a plurality of modulated stimulation rate intervals; and deliver a plurality of electrical stimulation pulses according to a header including at least one modulated stimulation rate interval and the plurality of modulated stimulation rate intervals of the data sequence to cause a modulated rate of activation of an excitable tissue a patient corresponding to the at least one modulated stimulation rate interval of the header and the plurality of modulated stimulation rate intervals of the data sequence, the modulated rate of activation detectable by a rate monitor for demodulation of the modulated rate of activation to the numerical value of the monitored variable.

* * * * *